United States Patent
Ushiroda et al.

(10) Patent No.: US 12,426,775 B2
(45) Date of Patent: Sep. 30, 2025

(54) MEDICAL OBSERVATION SYSTEM, CONTROL DEVICE, AND CONTROL METHOD

(71) Applicant: Sony Olympus Medical Solutions Inc., Tokyo (JP)

(72) Inventors: Hiroshi Ushiroda, Tokyo (JP); Kazuhiro Yamaguchi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 431 days.

(21) Appl. No.: 17/799,265

(22) PCT Filed: Dec. 4, 2020

(86) PCT No.: PCT/JP2020/045340
§ 371 (c)(1),
(2) Date: Aug. 12, 2022

(87) PCT Pub. No.: WO2021/186803
PCT Pub. Date: Sep. 23, 2021

(65) Prior Publication Data
US 2023/0066301 A1     Mar. 2, 2023

(30) Foreign Application Priority Data
Mar. 19, 2020   (JP) ................. 2020-048701

(51) Int. Cl.
*A61B 1/06* (2006.01)
*A61B 1/04* (2006.01)
(Continued)

(52) U.S. Cl.
CPC ............ *A61B 1/0655* (2022.02); *A61B 1/043* (2013.01); *A61B 1/05* (2013.01); *A61B 1/0638* (2013.01);
(Continued)

(58) Field of Classification Search
CPC ..... A61B 1/0655; A61B 1/043; A61B 1/0638; A61B 1/0646; G06T 5/50; G02B 21/361
See application file for complete search history.

(56) References Cited

U.S. PATENT DOCUMENTS 4,559,557 A * 12/1985 Keyes ............... A61B 6/481
                                                    378/98.5
4,854,301 A *  8/1989 Nakajima ......... A61B 90/50
                                                    600/102

(Continued)

FOREIGN PATENT DOCUMENTS

JP    2008-49168 A    3/2008
JP    2009-160386 A   7/2009

(Continued)

OTHER PUBLICATIONS

International Search Report and Written Opinion mailed on Feb. 9, 2021, received for PCT Application PCT/JP2020/045340, filed on Dec. 4, 2020, 12 pages including English Translation.

*Primary Examiner* — Anh Tuan T Nguyen
*Assistant Examiner* — Jae Woo
(74) *Attorney, Agent, or Firm* — XSENSUS LLP

(57) ABSTRACT

Provided are a medical observation system, a control device, and a control method that are configured to prevent flickering of a portion to be observed of an object to be observed and reduce the size of the device. The medical observation system 1 includes an image sensor 212, a second control unit 94 that causes a light source device 3 to simultaneously emit second visible light and excitation light, and an image processing unit 91 that generates a fluorescence image based on a first pixel value that is output from a pixel in which a first filter is arranged and that is contained in image data and a background image based on a second pixel value that is output from a pixel in which a second filter is arranged.

20 Claims, 12 Drawing Sheets

(51) Int. Cl.
  *A61B 1/05* (2006.01)
  *G06T 5/50* (2006.01)
  *G06T 11/00* (2006.01)
(52) U.S. Cl.
  CPC .............. *A61B 1/0646* (2013.01); *G06T 5/50* (2013.01); *G06T 11/001* (2013.01)

(56) References Cited

U.S. PATENT DOCUMENTS

| | | | | |
|---|---|---|---|---|
| 5,846,221 | A * | 12/1998 | Snoke | A61M 25/0136 604/533 |
| 8,451,328 | B2 * | 5/2013 | Yoshino | A61B 1/0655 348/222.1 |
| 8,488,239 | B2 * | 7/2013 | Nakamura | G02B 7/001 359/388 |
| 11,109,748 | B2 * | 9/2021 | Okada | A61B 1/00133 |
| 2002/0103418 | A1 * | 8/2002 | Maeda | A61B 1/0016 600/152 |
| 2009/0147999 | A1 * | 6/2009 | Maeda | A61B 5/0071 382/106 |
| 2009/0289200 | A1 * | 11/2009 | Ishii | A61B 1/0655 250/459.1 |
| 2010/0245616 | A1 * | 9/2010 | Yoshino | A61B 1/0646 382/163 |
| 2015/0297073 | A1 * | 10/2015 | Nguyen | A61B 1/07 600/103 |
| 2015/0381909 | A1 * | 12/2015 | Butte | A61B 1/0669 250/578.1 |
| 2018/0153386 | A1 * | 6/2018 | Omori | A61B 1/0005 |
| 2018/0210188 | A1 * | 7/2018 | Ganapati | A61B 1/0638 |
| 2019/0216325 | A1 * | 7/2019 | Ouyang | G02B 23/2461 |
| 2021/0290035 | A1 * | 9/2021 | Michihata | A61B 1/0638 |
| 2021/0294084 | A1 * | 9/2021 | Yamaguchi | A61B 1/000095 |
| 2021/0297575 | A1 * | 9/2021 | Michihata | A61B 1/0638 |

FOREIGN PATENT DOCUMENTS

| | | |
|---|---|---|
| JP | 2016-87062 A | 5/2016 |
| JP | 2016-198634 A | 12/2016 |
| JP | 2017-29471 A | 2/2017 |
| JP | 2017-104567 A | 6/2017 |
| JP | 2018-504628 A | 2/2018 |
| JP | 2018-534584 A | 11/2018 |
| JP | 2019-93157 A | 6/2019 |
| JP | 2019-168423 A | 10/2019 |
| WO | 2017/038015 A1 | 3/2017 |
| WO | 2018/179564 A1 | 10/2018 |
| WO | WO-2020112724 A1 | 6/2020 |

* cited by examiner

MEDICAL OBSERVATION SYSTEM, CONTROL DEVICE, AND CONTROL METHOD

CROSS-REFERENCE TO RELATED APPLICATIONS

The present application is based on PCT filing PCT/JP2020/045340, filed Dec. 4, 2020, which claims priority to JP 2020-048701, filed Mar. 19, 2020, the entire contents of each are incorporated herein by reference.

FIELD

The present disclosure relates to a medical observation system, a control device, and a control method that capture an object to be observed to generate image data.

BACKGROUND

In a conventional surgical microscope, there is known a technique of providing, on an incident side of one of two image sensors, a cut filter that blocks excitation light for exciting a fluorescent substance and that transmits fluorescence from the fluorescent substance to perform observation with visible light and observation with infrared light (e.g., see Patent Literature 1).

Furthermore, a medical observation system is provided with an image sensor having a Bayer array and an image sensor having sensitivity to infrared light, emits white light and infrared light, and acquires a normal image with white light and an infrared fluorescence image with infrared light (e.g., see Patent Literature 2).

CITATION LIST

Patent Literature

Patent Literature 1: JP 2008-49168 A
Patent Literature 2: JP 2016-087062 A

SUMMARY

Technical Problem

However, in Patent Literature 1 described above, there is a problem that observation with visible light and observation with infrared light using two image sensors makes it difficult to provide a device reduced in size.

In addition, in Patent Literature 2 described above, there is a problem that alternate emission of the white light and the infrared light flickers a portion to be observed of the object to be observed.

The present disclosure has been made in view of the above, and an object thereof is to provide a medical observation system, a control device, and a control method that are configured to prevent flickering of a portion to be observed of an object to be observed to provide a device reduced in size.

Solution to Problem

To solve the above-described problem and achieve the object, a medical observation system according to the present disclosure includes: a light source device configured to emit, to an object, first visible light and second visible light having different wavelength bands, and excitation light exciting a fluorescent substance and causing emission of fluorescence; an image sensor including: a pixel portion including a plurality of pixels; a first filter configured to transmit the first visible light and the fluorescence; and a second filter configured to transmit the second visible light and the fluorescence, each of the first filter and the second filter being provided on a light receiving surface of each of the plurality of pixels, the image sensor being configured to capture at least one of reflected light of at least one of the first visible light and the second visible light reflected from the object and the fluorescence to generate image data; a control unit configured to control the light source device to simultaneously emit the second visible light and the excitation light; and an image processing unit configured to generate a fluorescence image based on a first pixel value included in the image data and output from a pixel in which the first filter is arranged, and a background image based on a second pixel value output from a pixel in which the second filter is arranged.

Moreover, a medical observation system according to the present disclosure includes: a light source device configured to emit, to an object, first visible light and second visible light having different wavelength bands, and excitation light exciting a fluorescent substance and causing emission of fluorescence; a dichroic prism configured to split reflected light of at least one of the first visible light and the second visible light reflected from the object and the fluorescence into a plurality of wavelength bands; a plurality of image sensors configured to receive light beams of the plurality of wavelength bands split by the dichroic prism and generate a plurality of pieces of image data; a control unit configured to control the light source device to simultaneously emit the second visible light and the excitation light; and an image processing unit configured to generate a background image and a fluorescence image based on the plurality of pieces of image data.

A control device according to the present disclosure for controlling a light source device and a medical imaging device, the light source device being configured to emit, to an object, first visible light and second visible light having different wavelength bands, and excitation light exciting a fluorescent substance and causing emission of fluorescence, the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, includes: a control unit configured to control the light source device to simultaneously emit the second visible light and the excitation light; and an image processing unit configured to generate a fluorescence image based on a first pixel value included in the image data and output from a pixel in which the first filter is arranged, and a background image based on a second pixel value output from a pixel in which the second filter is arranged.

A control method according to the present disclosure executed by a control device for controlling a light source device and a medical imaging device, the light source device being configured to emit, to an object, first visible light and second visible light having different wavelength bands, and excitation light exciting a fluorescent substance and causing emission of fluorescence, the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, includes: controlling the light source device to simultaneously emit the second visible light and the excitation light; and generating a fluorescence image based on a first pixel value included in the image data and output from a pixel in which the first filter is arranged, and a background image based on a second pixel value output from a pixel in which the second filter is arranged.

Advantageous Effects of Invention

According to the present disclosure, the flicker of the portion to be observed can be effectively prevented and the size of the device can be effectively reduced.

DESCRIPTION OF EMBODIMENTS

Figure 1:
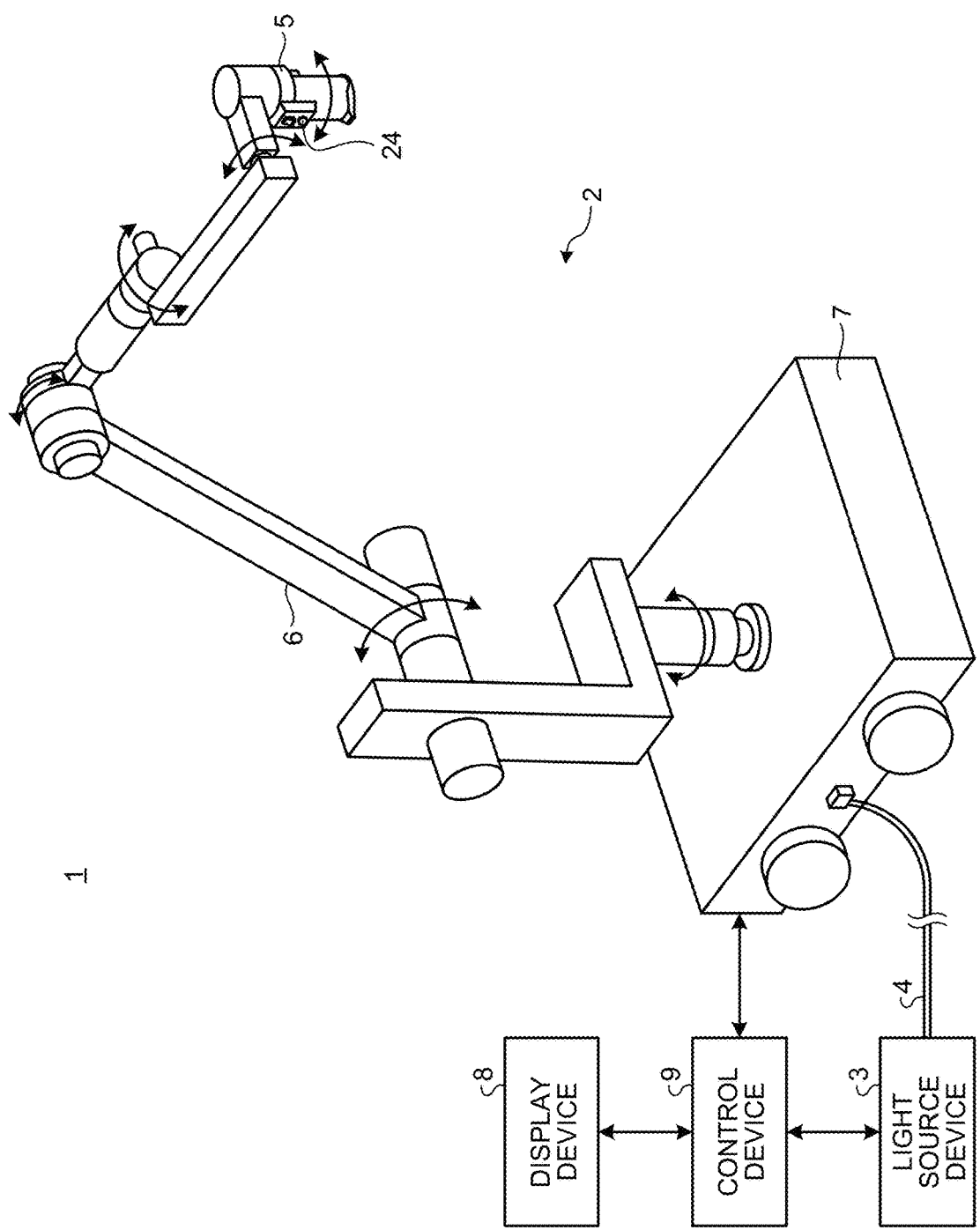
FIG. 1 is a diagram illustrating the overall configuration of a medical observation system according to a first embodiment.

Modes for carrying out the present disclosure (hereinafter, referred to as "embodiments") will be described below in detail with reference to the drawings. Note that the present disclosure is not limited to the following embodiments. In addition, the drawings referred to in the following descriptions are merely schematically illustrated in shape, size, and positional relationship to the extent of understanding the contents of the present disclosure. In other words, the present disclosure is not limited only to the shapes, sizes, and positional relationships exemplified in the drawings.

First Embodiment

[Schematic Configuration of Medical Observation System]

FIG. 1 is a diagram illustrating the overall configuration of a medical observation system according to a first embodiment. A medical observation system 1 illustrated in FIG. 1 includes a medical observation apparatus 2, a light source device 3, a display device 8, and a control device 9, the medical observation apparatus 2 has a function as a microscope to magnify and observe a minute portion of an object to be observed, the light source device 3 supplies illumination light to the observation apparatus 2 via a light guide 4 including optical fiber or the like, the display device 8 displays an image on the basis of image data captured by the observation apparatus 2, and the control device 9 integrally controls the operation of the medical observation system 1.

[Schematic Configuration of Observation Apparatus]

First, a schematic configuration of the observation apparatus 2 will be described. The observation apparatus 2 includes a microscope unit 5, a support unit 6, and a base portion 7. The microscope unit 5 observes the minute portion of the object to be observed, the support unit 6 is connected to a base end portion of the microscope unit 5 to turnably support the microscope unit 5, and the base portion 7 turnably holds a base end portion of the support unit 6 and is configured to move on a floor surface.

The microscope unit 5 has a columnar appearance and internally includes an optical system, an image sensor (not illustrated), and a light emitting unit (not illustrated). The optical system has a zoom function and a focus function, the image sensor receives an object image formed by the optical system and performs photoelectric conversion to generate the image data, and the light emitting unit emits the illumination light to the object to be observed. Furthermore, the microscope unit 5 has a side surface that is provided with various switches that constitute an input unit 24 receiving inputs of operation instructions for the observation apparatus 2. The microscope unit 5 has an opening surface at a lower end and the opening surface is provided with a cover glass (not illustrated) that protects the optical system and the like positioned on the inside. A user such as an operator, for example, moves the microscope unit 5, changes the angle of the microscope unit 5, changes modes of the observation apparatus 2, or performs zoom or focus operation, while operating the various switches with the microscope unit 5 held. Note that the shape of the microscope unit 5 is not limited to the cylindrical shape but may be, for example, a polygonal cylindrical shape.

Under the control of the control device 9, the light source device 3 supplies, to the observation apparatus 2 via the light guide 4, illumination light of at least one of white light including light in a red wavelength band, light in a green wavelength band, and light in a blue wavelength band, and infrared light. The light source device 3 includes a discharge lamp such as a xenon lamp or metal halide lamp, a solid-state light emitting device such as a light emitting diode (LED) or a laser diode (LD), a light emitting member such as a halogen lamp, or the like.

The display device 8 displays an image to be displayed that is generated by the control device 9 or various types of information about the medical observation system. The display device 8 includes liquid crystal, organic electro luminescence (EL), or the like. The display device 8 displays a 2D image or 3D image.

The control device 9 integrally controls the respective units of the medical observation system 1. The control device 9 is implemented by using a memory, and a general-purpose processor such as a central processing unit (CPU) or a processor including hardware such as various arithmetic circuits performing specific functions, including an application specific integrated circuit (ASIC), graphics processing unit (GPU), and the like. Furthermore, the control device 9 may include a field programmable gate array (FPGA: not illustrated) that is a kind of programmable integrated circuit. Note that when the FPGA is included, a memory storing configuration data may be provided so that the FPGA as the programmable integrated circuit is configured on the basis of the configuration data read from the memory. Note that the configuration of the control device 9 will be described in detail later.

[Functional Configuration of Medical Observation System]

Figure 2:
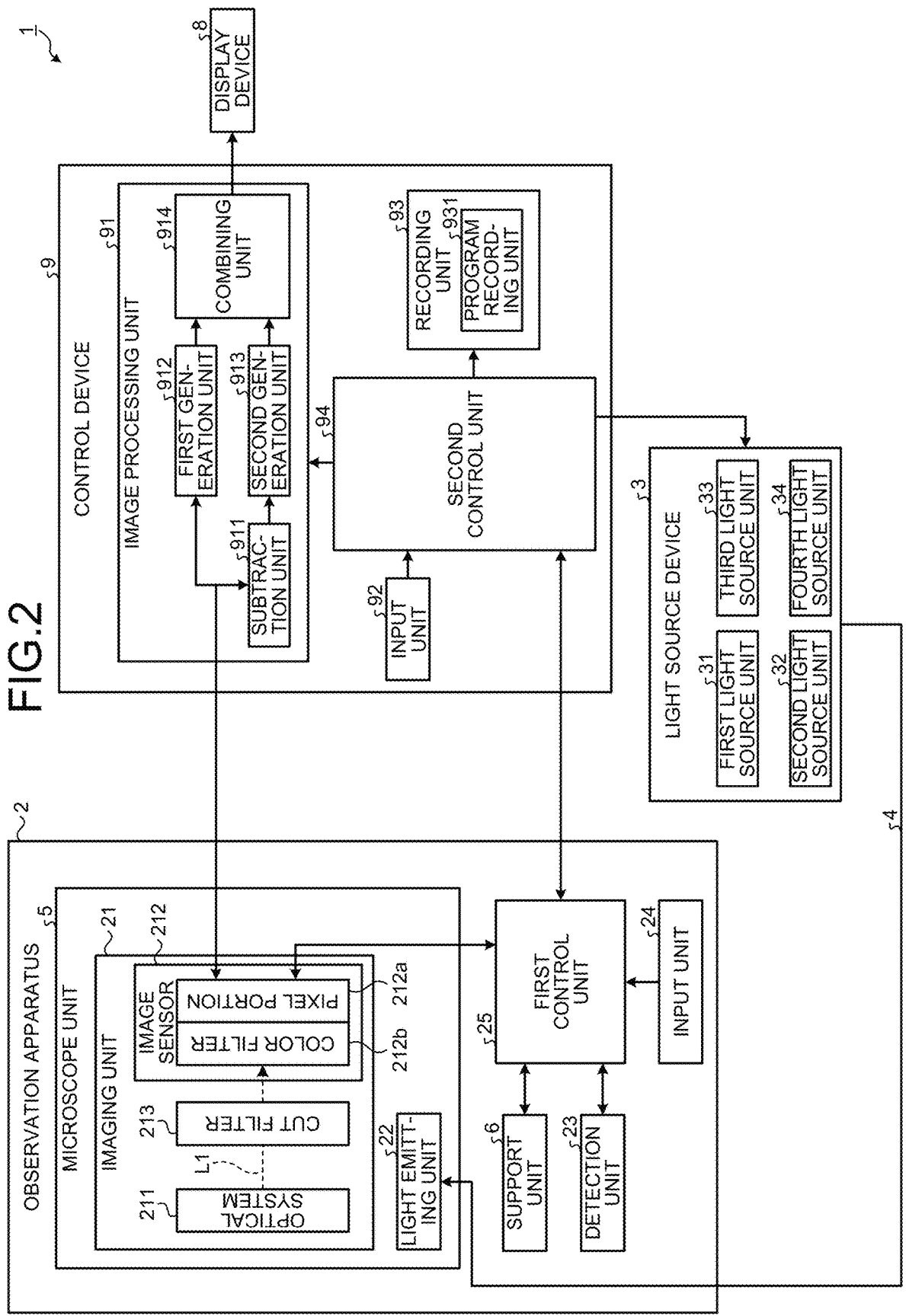
FIG. 2 is a block diagram illustrating a functional configuration of the medical observation system according to the first embodiment.

Next, a functional configuration of the medical observation system 1 will be described. FIG. 2 is a block diagram illustrating the functional configuration of the medical observation system 1.

[Functional Configuration of Observation Apparatus]

First, a functional configuration of the observation apparatus 2 will be described.

The observation apparatus 2 includes the microscope unit 5, a detection unit 23, the input unit 24, and a first control unit 25.

The microscope unit 5 includes an imaging unit 21 and a light emitting unit 22. The imaging unit 21 magnifies an image of the object to be observed that is an observation target to generate the image data, and the light emitting unit 22 emits, to the object to be observed, the illumination light supplied from the light source device 3.

The imaging unit 21 includes an optical system 211, an image sensor 212, and a cut filter 213. Note that the imaging unit 21 functions as a medical imaging device according to the first embodiment.

The optical system 211 has a zoom and focus function and forms the object image on a light receiving surface of the image sensor 212 via the cut filter 213. The optical system 211 is implemented by using one or a plurality of lenses, a motor moving the lenses along an optical path L1, and the like.

The image sensor 212 receives the object image formed by the optical system 211 via the cut filter 213, and performs photoelectric conversion to generate the image data (RAW data). The image sensor 212 is implemented by using an image sensor, such as a charge coupled device (CCD) or complementary metal oxide semiconductor (CMOS). The image sensor 212 includes a pixel portion 212a and a color filter 212b.

Figure 3:
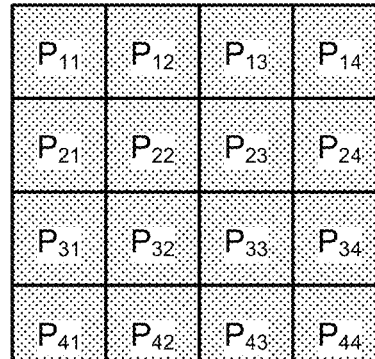
FIG. 3 is a diagram schematically illustrating a configuration of a pixel portion according to the first embodiment.

FIG. 3 is a diagram schematically illustrating a configuration of the pixel portion 212a. As illustrated in FIG. 3, in the pixel portion 212a, a plurality of pixels $P_{n,m}$ (n=an integer of 1 or more and m=an integer of 1 or more), such as photodiodes, accumulating electric charges according to an amount of light is arranged in a two-dimensional matrix. Under the control of the first control unit 25, the pixel portion 212a reads an image signal, as the image data, from a pixel $P_{n,m}$ in any read area set as a read target, from among the plurality of pixels $P_{n,m}$, and outputs the image data to the control device 9. Specifically, the image data generated by the pixel portion 212a is transmitted to the control device 9 via a transmission cable. Note that the image data generated by the pixel portion 212a may be subjected to E/0 conversion so as to be transmitted to the control device 9 using an optical signal.

Figure 4:
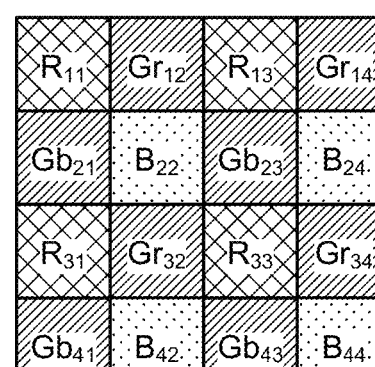
FIG. 4 is a diagram schematically illustrating a configuration of a color filter according to the first embodiment.

FIG. 4 is a diagram schematically illustrating a configuration of the color filter 212b. The color filter 212b illustrated in FIG. 4 includes a Bayer array having 2 ×2 filters as one unit. The color filter 212b includes a filter R that transmits light in a red wavelength band, two filters G (a filter Gr and a filter Gb) that each transmit light in a green wavelength band, and a filter B that transmits light in a blue wavelength band.

In the following description, a pixel $P_{n,m}$ having a light receiving surface on which the filter R is arranged is referred to as an R pixel, a pixel $P_{n,m+1}$ having a light receiving surface on which the filter Gr is arranged is referred to as a Gr pixel, a pixel $P_{n+1,m}$ having a light receiving surface on which the filter Gb is arranged is referred to as a Gb pixel (hereinafter, the Gr pixel and the Gb pixel are collectively referred to as a G pixel), and a pixel $P_{n+1,m+1}$ having a light receiving surface on which the filter B is arranged is referred to as a B pixel. Furthermore, in the first embodiment, the filter R functions as a first filter that transmits light (first visible light) in a red wavelength band and fluorescence, each of the filters G functions as a second filter that transmits light (second visible light) in a green wavelength band and fluorescence, and the filter B functions as a third filter that transmits light (third visible light) in a blue wavelength band and fluorescence. In other words, a pixel value of the R pixel includes components of reflected red light and fluorescence, a pixel value of each of the G pixels (the Gr pixel and the Gb pixel) includes components of reflected green light and fluorescence, and a pixel value of the B pixel includes components of reflected blue light and fluorescence.

The cut filter 213 is arranged on the optical path L1 between the optical system 211 and the image sensor 212. The cut filter 213 blocks light having a wavelength component (e.g., 740±10 nm) of excitation light included in the object image formed by the optical system 211 and transmits light having a wavelength component of light other than the excitation light.

Figure 5:
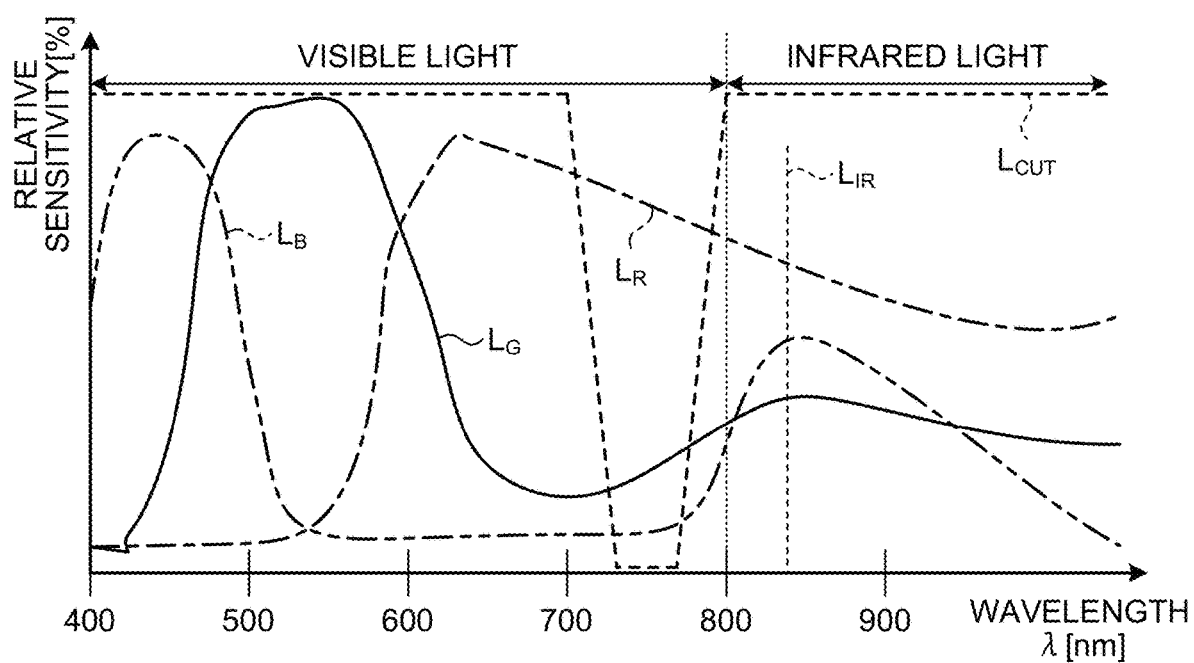
FIG. 5 is a graph schematically illustrating the sensitivity of an image sensor to wavelength bands after passing through the color filter according to the first embodiment.

Here, a spectral characteristic of each pixel will be described. FIG. 5 is a graph schematically illustrating the sensitivity of the image sensor to wavelength bands after passing through the color filter. In FIG. 5, the horizontal axis represents wavelength (nm) and the vertical axis represents spectral characteristic. Furthermore, in FIG. 5, a curve $L_B$ represents the spectral characteristic of the B pixel, a curve $L_G$ represents the spectral characteristic of the G pixel, a curve $L_R$ represents the spectral characteristic of the R pixel, and a straight line $L_{IR}$ represents the wavelength band of fluorescence generated by irradiating a fluorescent substance with the excitation light. A curve $L_{CUT}$ represents a transmission characteristic of the cut filter 213.

As represented by the curve $L_B$ and the straight line $L_{IR}$ of FIG. 5, the B pixel is sensitive to the light in a blue wavelength band (435 nm to 480 nm) (hereinafter, simply referred to as "blue light") and is sensitive to the fluorescence of a wavelength band (830±10 nm) generated by irradiating the fluorescent substance with the excitation light. Furthermore, as represented by the curve $L_G$ and the straight line $L_{IR}$ of FIG. 5, the G pixel (the Gr pixel and the Gb pixel) is sensitive to light in a green wavelength band (500 nm to 560 nm) (hereinafter, simply referred to as "green light") and is sensitive to the fluorescence of the wavelength band (830±10 nm) generated by irradiating the fluorescent substance with the excitation light. Furthermore, as represented by the curve $L_R$ and the straight line $L_{IR}$ of FIG. 5, the R pixel is sensitive to light in a red wavelength band (610 nm to 750 nm) (hereinafter, simply referred to as "red light") and is sensitive to the fluorescence of the wavelength band (830±10 nm) generated by irradiating the fluorescent substance with the excitation light.

The light emitting unit 22 includes an illumination optical system constituted by using one or more lenses. The light emitting unit 22 emits the illumination light in a direction the same as an imaging direction of the imaging unit 21, the illumination light being at least one of the white light supplied from the light source device 3 via the light guide 4, the light in a red wavelength band, the light in a green wavelength band, the light in a blue wavelength band, and the infrared light. Note that the light emitting unit 22 may be provided with a light emitting diode (LED), a laser light source, or the like at the microscope unit 5 to omit optical transmission via the light guide or the like.

The detection unit 23 sequentially detects state information about the observation apparatus 2. The state information about the observation apparatus 2 includes information about the position, focus, and zoom of the imaging unit 21. The detection unit 23 includes various sensors to detect these types of information.

The input unit 24 receives the input of the operation instructions for the imaging unit 21. The input unit 24 includes a focus switch and a zoom switch that receive input of instructions for focus and zoom operations in the imaging unit 21, an electric scrolling mode switch that receives input of an instruction for an electric scrolling mode, a mode changeover switch that receives input of an instruction for changing observation modes of the medical observation system 1, and the like As illustrated in FIG. 1, the various switches, buttons, and the like constituting the input unit 24 are provided on the side surface of the microscope unit 5.

The first control unit 25 controls the operation of the imaging unit 21 in response to the operation instruction received by the input unit 24 or an operation instruction input from the control device 9 which is described later. Furthermore, the first control unit 25 integrally controls the observation apparatus 2 in cooperation with a second control unit 94 of the control device 9 which is described later. The first control unit 25 includes a memory, and a processor such as CPU, FPGA, or ASIC.

[Configuration of Light Source Device]

A configuration of the light source device 3 will be described next.

The light source device 3 includes a first light source unit 31, a second light source unit 32, a third light source unit 33, and a fourth light source unit 34.

Under the control of the control device 9, the first light source unit 31 supplies the red light to the light emitting unit 22 of the observation apparatus 2 via the light guide 4. The first light source unit 31 is implemented by using a red LED or the like.

Under the control of the control device 9, the second light source unit 32 supplies the green light to the light emitting unit 22 of the observation apparatus 2 via the light guide 4. The second light source unit 32 is implemented by using a green LED or the like.

Under the control of the control device 9, the third light source unit 33 supplies the blue light to the light emitting unit 22 of the observation apparatus 2 via the light guide 4. The third light source unit 33 is implemented by using a blue LED or the like.

The fourth light source unit 34 supplies the infrared light that excites the fluorescent substance, to the light emitting unit 22 of the observation apparatus 2 via the light guide 4. Under the control of the control device 9, the fourth light source unit 34 supplies the infrared light (wavelength band of 740±10 nm) that functions as the excitation light exciting the fluorescent substance. The second light source unit 32 includes a semiconductor laser device that is configured to emit infrared light (700 to 1000 nm) used for indocyanine green (ICG) observation, a filter that transmits only a predetermined wavelength band (wavelength band of 740±10 nm), and the like. Note that in the following, infrared light is described as the excitation light, but the excitation light is not limited to the infrared light but may be, for example, light (wavelength band of 415±10 nm) used for photo dynamic diagnosis (PDD) observation of fluorescence of a photosensitive substance, such as hematoporphyrin derivative, accumulated in tumor tissue in advance, and light (wavelength band of 390 to 470 nm+wavelength band of 540 to 560 nm) used for auto fluorescence imaging (AFI) observation of observing auto fluorescence from the fluorescent substance such as collagen.

[Configuration of Control Device]

Next, a functional configuration of the control device 9 will be described.

The control device 9 includes an image processing unit 91, an input unit 92, a recording unit 93, and the second control unit 94.

The image processing unit 91 performs various types of image processing on the image data transmitted from the observation apparatus 2 to generate the image to be displayed (video data) that is displayed by the display device 8. Here, examples of the image processing include various types of image processing and the like, such as color correction, color enhancement, and contour enhancement. The image processing unit 91 is implemented by using a memory and a processor such as a graphics processing unit (GPU), ASIC, or FPGA. The image processing unit 91 includes at least a subtraction unit 911, a first generation unit 912, a second generation unit 913, and a combining unit 914.

The subtraction unit 911 subtracts a first pixel value (R pixel) that is output from a pixel (R pixel) in which the first filter (filter R) is arranged, from a second pixel value that is output from a pixel (B pixel or G pixel) in which the second or third filter (filter G or filter B) is arranged and that is contained in the image data input from the imaging unit 21, and outputs a result of the subtraction to the second generation unit 913. Specifically, the subtraction unit 911 may subtract, from the first pixel value, a multiplication result obtained by multiplying a value obtained by dividing a spectral sensitivity of the second filter to a fluorescence wavelength by a spectral sensitivity of the first filter to the fluorescence wavelength by the first pixel value, and may output this subtraction result to the second generation unit

913. In other words, the subtraction unit 911 may change the second pixel value on the basis of the first pixel value and output a changed result (changed second pixel value) to the second generation unit 913. Note that a calculation method by the subtraction unit 911 will be described later.

Under the control of the second control unit 94, the first generation unit 912 generates a fluorescence image, on the basis of the first pixel value that is output from the pixel (R pixel) in which the first filter (filter R) is arranged and that is contained in the image data input from the imaging unit 21, and outputs the fluorescence image to the combining unit 914. Specifically, on the basis of the pixel value of the R pixel contained in the image data, the first generation unit 912 interpolate the pixel values of the B pixel and G pixel, generates the fluorescence image, and outputs the fluorescence image to the combining unit 914. Furthermore, the first generation unit 912 performs colorization for the fluorescence image. Specifically, the first generation unit 912 colorizes the fluorescence image by a tone conversion process or the like on the basis of a brightness value of the fluorescence image, and outputs the colored fluorescence image to the combining unit 914. For example, the first generation unit 912 performs the colorization to color a fluorescent area green on the basis of the brightness value of the fluorescence image. Note that the first generation unit 912 may set a color to be applied to the fluorescence image, on the basis of an instruction signal that is input from the input unit 92 via the second control unit 94 to specify the color of the fluorescent area of the fluorescence image.

Under the control of the second control unit 94, the second generation unit 913 generates a background image, on the basis of the second pixel value and a third pixel value that are output from the pixels (G pixel and B pixel) in which the second and third filters (filter G and filter B) are arranged and that are contained in the image data input from the imaging unit 21, and outputs the background image to the combining unit 914. Specifically, the second generation unit 913 generates the background image on the basis of a result of the input from the subtraction unit 911. Furthermore, the second generation unit 913 may perform grayscale processing on the background image and output the background image to the combining unit 914. For example, the second generation unit 913 performs saturation reduction processing to reduce the saturation of the background image and outputs the background image converted into a grayscale image to the combining unit 914.

The combining unit 914 generates a composite image in which the fluorescence image input from the first generation unit 912 and the background image input from the second generation unit 913 are combined, and outputs the composite image to the display device 8. Specifically, the combining unit 914 may generate the composite image by combining the fluorescence image with the background image at a predetermined ratio (e.g., 1:1).

The input unit 92 is implemented using a user interface such as a keyboard, mouse, touch panel, or foot switch to receive input of various types of information.

The recording unit 93 includes a program recording unit 931 that uses a semiconductor memory such as a flash memory or dynamic random access memory (DRAM) and that temporarily records various programs executed by the medical observation system 1 and data being processed.

The second control unit 94 integrally controls the respective units of the medical observation system 1. The second control unit 94 is implemented by using a general-purpose processor, such as a CPU, having an internal memory (not illustrated) in which a program is recorded or a dedicated processor such as various arithmetic circuits performing specific functions, including ASIC, FPGA, and the like. Furthermore, the second control unit 94 may include an FPGA that is a type of a programmable integrated circuit. Note that when the FPGA is included, a memory storing configuration data may be provided so that the FPGA as the programmable integrated circuit is configured on the basis of the configuration data read from the memory. The second control unit 94 causes the light source device 3 to emit the first and second visible light in different wavelength bands and excitation light exciting the fluorescent substance to cause emission of the fluorescence, to the object. Furthermore, the second control unit 94 causes the light source device 3 to simultaneously emit the second visible light and the excitation light to the object. Specifically, when the medical observation system 1 is in a first observation mode, the second control unit 94 causes the light source device 3 to emit the first visible light and the second visible light, and when the medical observation system 1 is in a second observation mode, the second control unit 94 causes the light source device 3 to emit the second visible light and the excitation light. Here, the first observation mode is a white light observation mode in which white light is emitted to the object. Furthermore, the second observation mode is a fluorescence observation mode for observation of the fluorescence. More specifically, the second control unit 94 causes the light source device 3 to simultaneously emit visible light including at least one of the green light and the blue light and the excitation light exciting the fluorescent substance to cause the emission of fluorescence. Furthermore, the second control unit 94 causes the microscope unit 5 to capture reflected light of visible light reflected from the object and the fluorescence and generate the image data.

[Process Performed by Medical Observation System]

Figure 7:
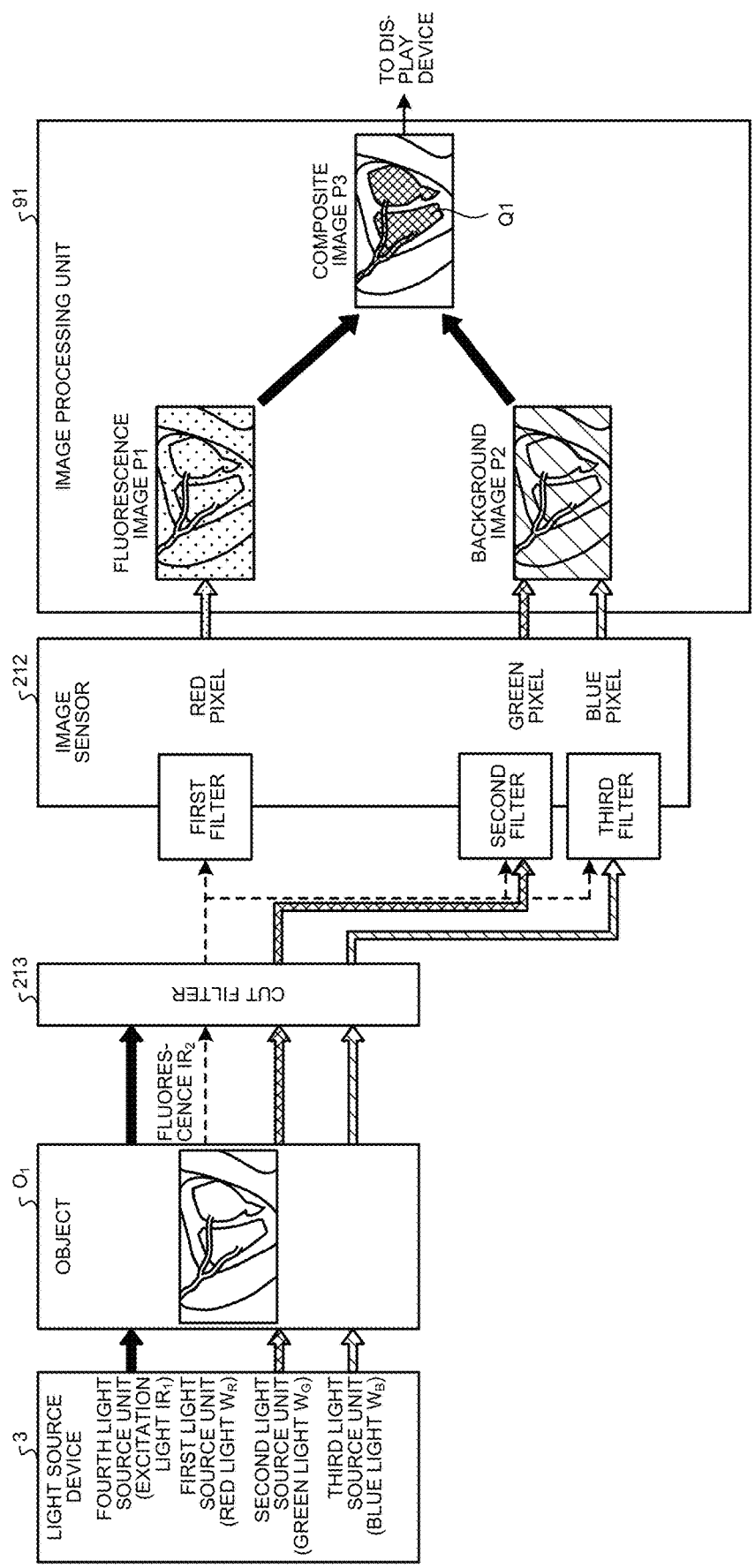
FIG. 7 is a diagram schematically illustrating the outline of a process in a fluorescence observation mode performed by the medical observation system according to the first embodiment.

Next, a process performed by the medical observation system 1 will be described. FIG. 7 is a flowchart illustrating the outline of the process performed by the medical observation system 1. Note that, in the following, to simplify the description, the white light observation mode and the fluorescence observation mode of a plurality of observation modes that can be performed by the medical observation system 1 will be described.

As illustrated in FIG. 7, the second control unit 94 determines whether the medical observation system 1 is set to the white light observation mode in which the white light is emitted to the object (Step S101). When the second control unit 94 determines that the medical observation system 1 is set to the white light observation mode in which the white light is emitted to the object (Step S101: Yes), the medical observation system 1 proceeds to Step S102 which is described later. On the other hand, when the second control unit 94 determines that the medical observation system 1 is set to the fluorescence observation mode in which the fluorescence is emitted to the object (Step S101: No), the medical observation system 1 proceeds to Step S107 which is described later.

In Step S102, the second control unit 94 causes the first light source unit 31, the second light source unit 32, and the third light source unit 33 to emit light, for emission of the white light. At this time, the fourth light source unit 34 is turned off.

Next, the second control unit 94 controls the first control unit 25 to cause the imaging unit 21 to receive light reflected from the object and capture an image of the object (Step S103).

Then, the image processing unit 91 performs various types of image processing on the image data input from the imaging unit 21 to generate a white light observation image (Step S104).

Subsequently, the display device 8 displays the white light observation image input from the image processing unit 91 (Step S105). This configuration makes it possible for the user such as a doctor to observe the object to be observed.

Then, the second control unit 94 determines whether an instruction signal to finish the observation of the object to be observed is input from the input unit 92 (Step S106). When it is determined by the second control unit 94 that the instruction signal to finish the observation of the object to be observed is input from the input unit 92 (Step S106: Yes), the medical observation system 1 finishes this process. On the other hand, when it is determined that no instruction signal to finish the observation of the object to be observed is input from the input unit 92 (Step S106: No), the medical observation system 1 returns to Step S101 described above.

In Step S107, the second control unit 94 determines whether the medical observation system 1 is set to at least the fluorescence observation mode in which the excitation light is emitted to the object (Step S101). When the second control unit 94 determines that the medical observation system 1 is set to at least the fluorescence observation mode in which the excitation light is emitted to the object (Step S107: Yes), the medical observation system 1 proceeds to Step S108 which is described later. On the other hand, when the second control unit 94 determines that the medical observation system 1 is not set to at least the fluorescence observation mode in which the excitation light is emitted to the object (Step S107: No), the medical observation system 1 proceeds to Step S106.

In Step S108, the second control unit 94 causes the fourth light source unit 34 to emit the excitation light to the object to which the fluorescent substance is administered, and further causes the second light source unit 32 and the third light source unit 33 to emit light to irradiate the object with green light and blue light (Step S108). Specifically, as illustrated in FIG. 7, the second control unit 94 causes the fourth light source unit 34 in the light source device 3 to emit light to irradiate the object $O_1$ to which the fluorescent substance has been administered, with excitation light $IR_1$. In this case, the second control unit 94 causes the second light source unit 32 and the third light source unit 33 to emit light simultaneously with the fourth light source unit 34 to irradiate the object $O_1$ with the excitation light $IR_1$, green light $W_G$, and blue light $W_B$.

Next, the second control unit 94 causes the imaging unit 21 to receive fluorescence $IR_2$ emitted from the object $O_1$ to capture an image, and further causes the imaging unit 21 to receive light returned from the object $O_1$ or the green light $W_G$ and the blue light $W_B$ that are reflected light from the object $O_1$ to capture an image (Step S109). In this case, as illustrated in FIG. 7, the cut filter 213 blocks the excitation light $IR_1$ reflected from the object $O_1$ and transmits the fluorescence $IR_2$, green light $W_G$, and blue light $W_B$ from the object $O_1$. Furthermore, in the respective pixels (the R pixel, G pixel, and B pixel) in the image sensor 212, the filters (the filter R, filter G, and filter B) are sensitive to the infrared range. Therefore, the light source device 3 emits no red light and the excitation light $IR_1$ is blocked by the cut filter 213, and thereby, only the fluorescence $IR_2$ is incident on the R pixel of the image sensor 212. Furthermore, the fluorescence $IR_2$ and the green light $W_G$ that is reflected from the object $O_1$ are incident on the G pixel of the image sensor 212. Furthermore, the fluorescence $IR_2$ and the blue light $W_B$ that is reflected from the object $O_1$ are incident on the B pixel of the image sensor 212. At this time, in the pixel value output from each of the G pixel and the B pixel, the fluorescence $IR_2$ incident on each of the G pixel and the B pixel has an intensity less than those of the reflected green light and the reflected blue light. Therefore, the reflected green light and the reflected blue light dominate. Furthermore, no red light is emitted from the light source device 3, and thus, in the pixel value of the R pixel, the fluorescence $IR_2$ dominates. In other words, the image processing unit 91 is configured to use an output value of the R pixel as an output value of the fluorescence $IR_2$, and output values of the G pixel and the B pixel can be used as output values of visible light (the reflected green light and reflected blue light).

Then, the subtraction unit 911 performs subtraction processing of subtracting the first pixel value that is output from a pixel (R pixel) in which the first filter (filter R) is arranged, from the second pixel value that is output from a pixel (G pixel or B pixel) in which the second or third filter (filter G or filter B) is arranged and that is contained in the image data input from the imaging unit 21 (Step S110).

Here, the subtraction processing performed by the subtraction unit 911 will be described in detail.

Figure 6:
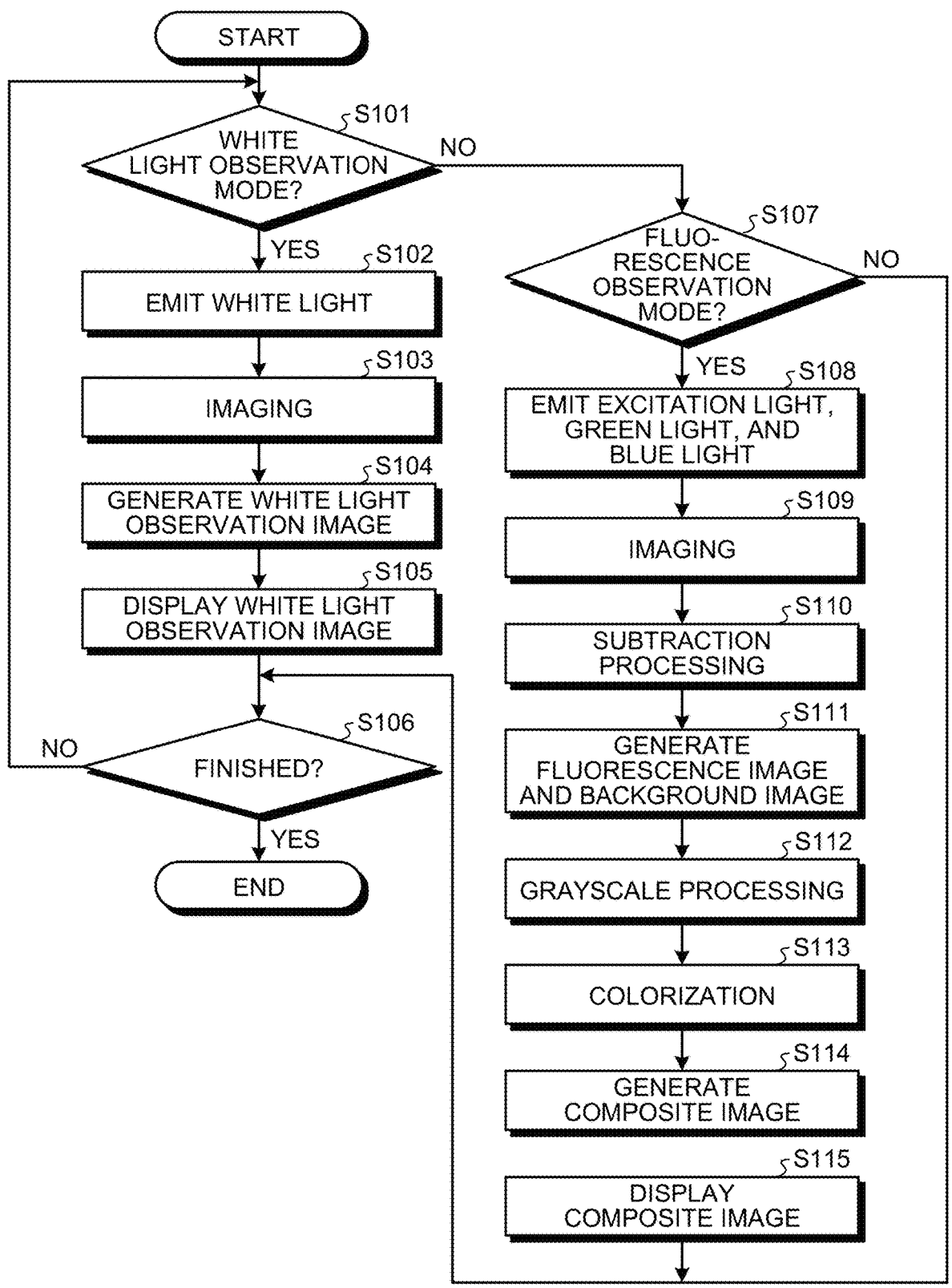
FIG. 6 is a flowchart illustrating the outline of a process performed by the medical observation system according to the first embodiment.

When the value of a fluorescent component included in the pixel value output from the Gr pixel (hereinafter, simply referred to as "IRgr"), the value of a fluorescent component included in the pixel value output from the Gb pixel (hereinafter, simply referred to as "IRgb"), and the value of a fluorescent component included in the pixel value output from the B pixel (hereinafter, simply referred to as "IRb") are obtained, a pixel value from which the fluorescent component of each pixel is removed can be estimated from the value of a fluorescent component included in the pixel value output from the R pixel (hereinafter, simply referred to as "IRr"). Specifically, when the spectral sensitivities of the R pixel, G pixels (Gr pixel and Gb pixel), and B pixel on the straight line $L_{IR}$ of FIG. 6 are defined as r, g, and b [%], the fluorescent components input to the R pixel, G pixels (Gr pixel and Gb pixel), and B pixel are considered to be constant. Therefore, the following formulas hold.

$$IRgr \approx IRgb \approx (g/r)^*IRr \qquad (1)$$

$$IRb \approx (b/r)^*IRr \qquad (2)$$

Furthermore, the light source device 3 emits no red light, and thus, the pixel value of the R pixel=IRr. Therefore, when the pixel value of the R pixel is R, the pixel value of the Gr pixel is Gr, the pixel value of the Gb pixel is Gb, and the pixel value of the B pixel is B, the subtraction unit 911 uses the following formulas (3) to (5) to calculate a value by subtracting the value of the fluorescent component from each of the pixel value (Gr=Gb) of the G pixel and the pixel value (B) of the B pixel.

$$\text{Pixel value of } Gr\text{pixel}=Gr-(g/r)^*IRgr \approx Gr-(g/r)^*R \qquad (3)$$

$$\text{Pixel value of } Gb\text{pixel}=Gb-(g/r)^*IRgb \approx Gb-(g/r)^*R \qquad (4)$$

$$\text{Pixel value of } B\text{pixel}=B-(b/r)^*IRb \approx B-(b/r)^*R \qquad (5)$$

Next, under the control of the second control unit 94, the image processing unit 91 generates the fluorescence image and a visible light image (Step S111). Specifically, the first generation unit 912 uses the pixel value of each R pixel contained in the image data input from the image sensor 212 to generate the fluorescence image. In this case, as illustrated in FIG. 7, the first generation unit 912 performs image processing by using the pixel value of each R pixel to generate a fluorescence image P1 in which the pixel value corresponding to the position of each of the B pixels and G pixels is interpolated. Note that, the fluorescence image P1 of FIG. 7 is hatched to express fluorescence, for convenience. Furthermore, the second generation unit 913 uses the pixel value of each of the G pixels and each of the B pixels contained in the image data that is input from the image sensor 212 and that is further input from the subtraction unit 911 to generate a background image P2. In this case, as illustrated in FIG. 7, the second generation unit 913 uses the pixel value of each of the G pixels and each of the B pixels to perform demosaic processing or the like, and generates the background image P2 in which the pixel value corresponding to the position of each R pixel is interpolated. Note that the background image P2 of FIG. 7 is hatched, for convenience.

Figure 8:
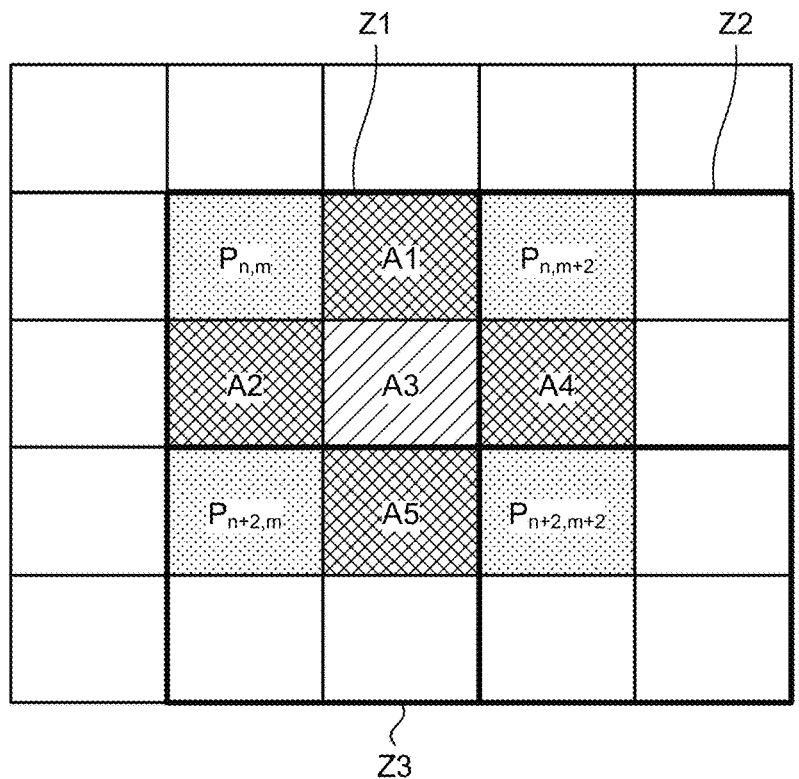
FIG. 8 is a diagram schematically illustrating a generation method to generate a fluorescence image by a first generation unit according to the first embodiment.

Here, a generation method to generate the fluorescence image P1 by the first generation unit 912 will be described. FIG. 8 is a diagram schematically illustrating the generation method to generate the fluorescence image P1 by the first generation unit 912.

As illustrated in FIG. 8, the first generation unit 912 interpolates the pixel value corresponding to the position of each of the B pixels and G pixels by replicating the pixel value of the R pixel (pixel $P_{n,m}$) as the pixel values of the B pixel (A3) and G pixels (A1 and A2) without using the pixel value of each of the B pixel (A3) and the G pixels (A1 and A2) in a unit Z1 in the Bayer array contained in the image data input from the image sensor 212. Likewise, in a unit Z2, the first generation unit 912 replicates the pixel value of the R pixel (pixel $P_{n,m+2}$) as the pixel values of the B pixel and G pixels (e.g., A4) to interpolate the pixel value corresponding to the position of each of the B pixel and G pixel. Furthermore, in a unit Z3, the first generation unit 912 replicates the pixel value of the R pixel (pixel $P_{n+2,m}$) as the pixel values of the B pixel and G pixel (e.g., A5) to interpolate the pixel value corresponding to the position of each of the B pixel and G pixel. In this way, the first generation unit 912 uses the pixel value of the R pixel in each unit to generate the fluorescence image P1 in which the pixel value corresponding to the position of each of the B pixel and G pixels is interpolated.

Figure 9:
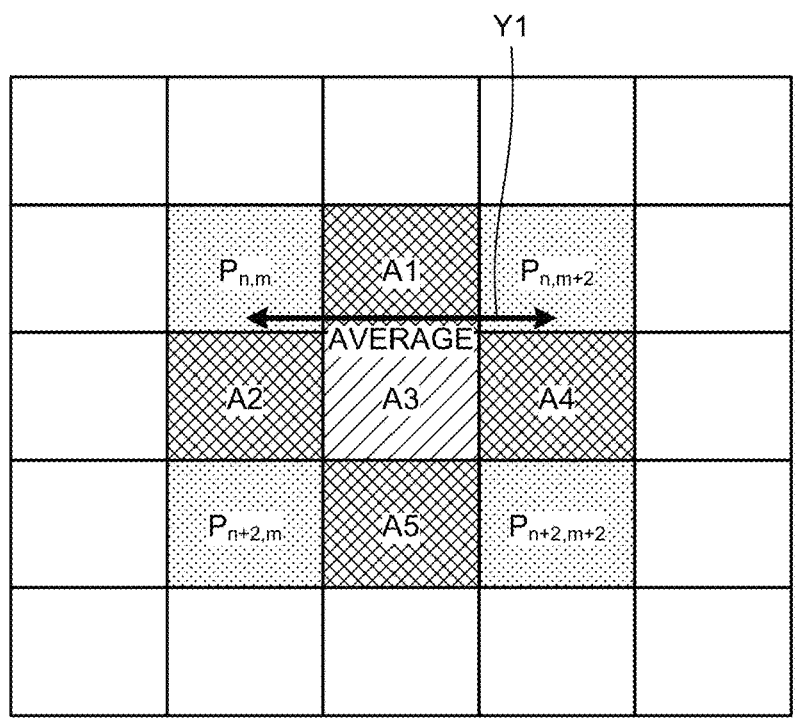
FIG. 9 is a schematic diagram illustrating another example of the generation method to generate the fluorescence image by the first generation unit according to the first embodiment.

FIG. 9 is a schematic diagram illustrating another example of the generation method to generate the fluorescence image P1 by the first generation unit 912.

As illustrated in FIG. 9, the first generation unit 912 uses an average value of the pixel values of adjacent R pixels to interpolate the pixel value corresponding to the position of each of the B pixel and G pixels, and generates the fluorescence image P1. Specifically, the first generation unit 912 sets the pixel value of the G pixel (A1) to the average value ((pixel value of pixel $P_{n,m}$)+(pixel value of pixel $P_{n,m+2}$)/2) of the pixel values of the R pixel (pixel $P_{n,m}$) and the R pixel (pixel $P_{n,m+2}$) that are adjacent to the G pixel. Likewise, the first generation unit 912 sets the pixel value of the G pixel (A2) to the average value ((pixel value of pixel $P_{n+2,m}$)+(pixel value of pixel $P_{n,m}$)/2) of the pixel values of the R pixel (pixel $P_{n,m}$) and the R pixel (pixel $P_{n+2,m}$) that are adjacent to the G pixel. Furthermore, the first generation unit 912 sets the pixel value of the B pixel (A3) to the average value ((pixel value of pixel $P_{n+2,m+2}$)+(pixel value of pixel $P_{n+2,m+2}$)/2) of the pixel values of the R pixel (pixel $P_{n,m}$) and the R pixel (pixel $P_{n+2,m+2}$) that are adjacent to the B pixel. In this way, the first generation unit 912 uses the average value of the pixel values of the adjacent R pixels to interpolate the pixel value corresponding to the position of each of the B pixel and G pixels, and generates the fluorescence image P1.

Figure 10:
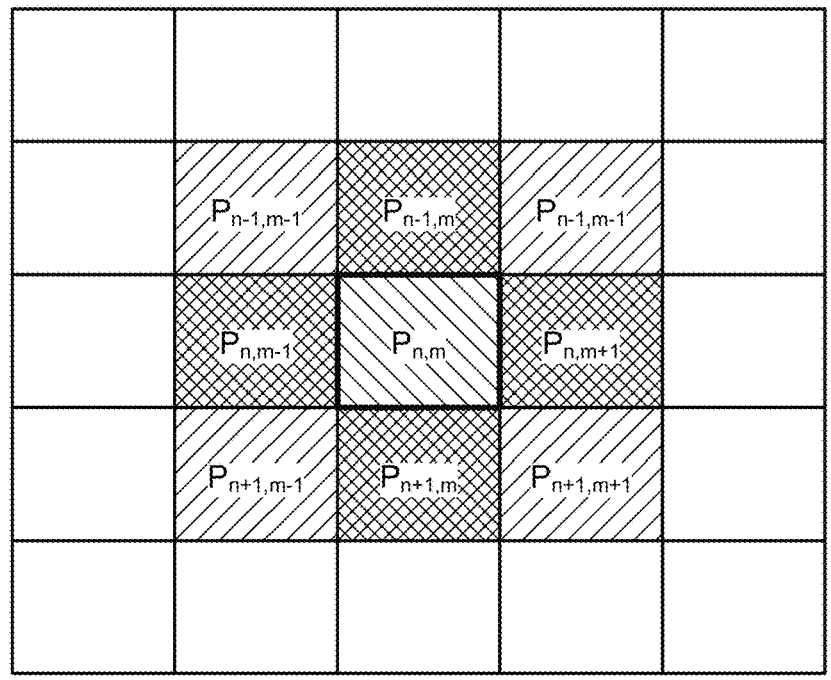
FIG. 10 is a diagram schematically illustrating a generation method to generate a background image by a second generation unit according to the first embodiment.

FIG. 10 is a diagram schematically illustrating a generation method to generate the background image P2 by the second generation unit 913.

As illustrated in FIG. 10, the second generation unit 913 considers the R pixel (pixel $P_{n,m}$) as black color (pixel value is 0), and performs demosaic processing to generate the background image P2.

Figure 11:
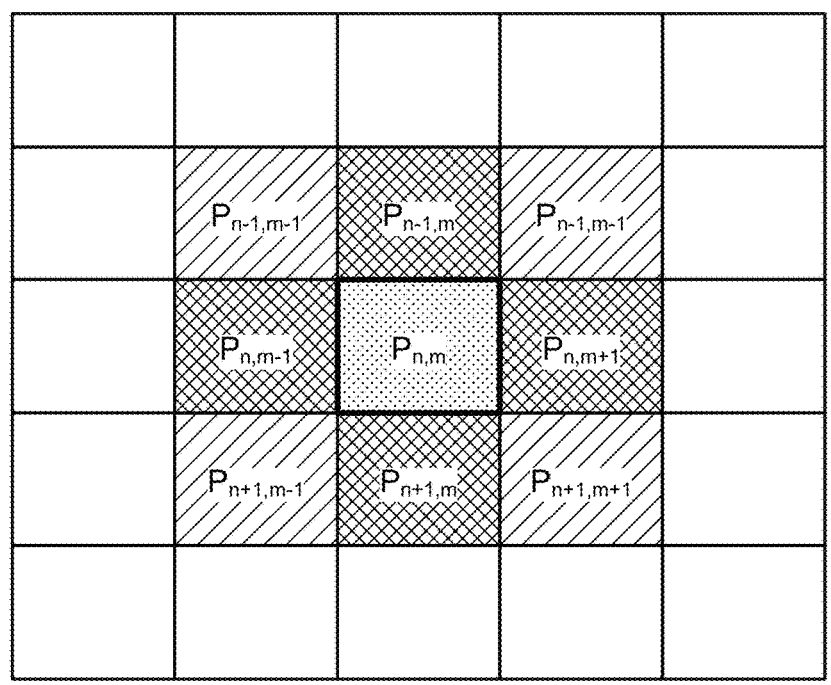
FIG. 11 is a diagram schematically illustrating another generation method to generate the background image by the second generation unit according to the first embodiment.

FIG. 11 is a diagram schematically illustrating another generation method to generate the background image P2 by the second generation unit 913.

As illustrated in FIG. 11, the second generation unit 913 interpolates the pixel value of the R pixel (pixel $P_{n,m}$) from the pixel values of surrounding pixels, and performs demosaic processing to generate the background image P2. For example, the second generation unit 913 sets the pixel value of the R pixel (pixel $P_{n,m}$) to an average value of the pixel values of eight surrounding pixels (pixel $P_{n-1,m-1}$, pixel $P_{n-1,m-1}$, pixel $P_{n-1,m+1}$, pixel $P_{n,m-1}$, pixel $P_{n,m+1}$, pixel $P_{n+1,m+1}$, pixel $P_{n+1,m}$, pixel $P_{n+1,m+1}$) or an average value of the pixel values of four surrounding G pixels (pixel $P_{n-1,m-1}$, pixel $P_{n,m-1}$, pixel $P_{n,m+1}$, pixel $P_{n+1,m}$).

Then, the second generation unit 913 performs grayscale processing on the background image P2 and outputs the background image P2 to the combining unit 914 (Step S112). Specifically, the second generation unit 913 may perform grayscale processing on the background image P2 to generate a grayscale image and output the grayscale image to the combining unit 914.

Then, the first generation unit 912 performs colorization for the fluorescence image P1 and outputs the fluorescence image P1 to the combining unit 914 (Step S113). Specifically, the first generation unit 912 colorizes the fluorescence image P1 by a tone conversion process or the like on the basis of the brightness value of the fluorescence image P1, and outputs the colored fluorescence image P1 to the combining unit 914. For example, the first generation unit 912 colorizes the fluorescence image P1 green.

Then, the combining unit 914 generates a composite image P3 in which the fluorescence image P1 generated by the first generation unit 912 and the background image P2 generated by the second generation unit 913 are combined (Step S114). Specifically, as illustrated in FIG. 8, the combining unit 914 generates the composite image P3 in which the fluorescence image P1 and the background image P2 are combined, and outputs the composite image P3 to the display device 8. In this case, the combining unit 914 generates the composite image P3 by combining the fluorescence image P1 with the background image P2 at a predetermined ratio (e.g., 1:1).

Then, the display device 8 displays the composite image P3 input from the combining unit 914 (Step S115). Thus, as illustrated in FIG. 8, the user such as the doctor can grasp the position of a fluorescent area Q1 by observing the composite image P3 displayed on the display device 8. After Step S112, the medical observation system 1 proceeds to Step S106.

According to the first embodiment described above, the second control unit 94 causes the light source device 3 to emit the second visible light and the excitation light, and the image processing unit 91 generates the background image based on the second pixel value that is output from the pixels (G pixel and B pixel) in which the second filter (filter G and filter B) is arranged and that is included in the image data and the fluorescence image based on the first pixel value that is output from the pixel (R pixel) in which the first filter (filter R) is arranged and that is included in the image data. In this method, the visible light and infrared excitation light are preferably simultaneously emitted from the light source device 3, and it is not necessary to alternately emit the visible light and the infrared excitation light. Therefore, flickering of a portion to be observed of the object to be observed can be prevented and the size of the device can be reduced.

Furthermore, according to the first embodiment, the fluorescence image P1 and the normal white light observation image are allowed to be generated by using one image sensor 212 having a normal Bayer array. Therefore, it is possible to observe the portion to be observed of the object to be observed while appropriately switching between the white light observation mode and the fluorescence observation mode, without using a special image sensor.

Furthermore, according to the first embodiment, after the grayscale processing on the background image, the image processing unit 91 combines the background image subjected to the grayscale processing with the fluorescence image. Therefore, it is possible to enhance the fluorescent area on the composite image.

Furthermore, according to the first embodiment, after monochromatization of the fluorescence image, the image processing unit 91 combines the monochromatized fluorescence image with the background image. Therefore, it is possible to enhance the fluorescent area on the composite image.

Furthermore, according to the first embodiment, in a case where the medical observation system 1 is set to the white light observation mode, the second control unit 94 causes the first light source unit 31, the second light source unit 32, and the third light source unit 33 to emit light for irradiation with white light, and in a case where the medical observation system 1 is set to the fluorescence observation mode, the second control unit 94 causes the second light source unit 32, the third light source unit 33, and the fourth light source unit 34 to emit light for simultaneous irradiation with visible light and excitation light. Therefore, it is possible to observe the portion to be observed of the object to be observed while appropriately switching between the white light observation mode and the fluorescence observation mode.

Furthermore, according to the first embodiment, the image processing unit 91 subtracts, from each of the second and third pixel values (pixel value of each of the G pixel and B pixel), the multiplication result obtained by multiplying the value obtained by dividing the spectral sensitivity of each of the second and third filters (filter G and filter B) to the fluorescence wavelength by the spectral sensitivity of the first filter (filter R) to the fluorescence wavelength by the first pixel value (pixel value of the R pixel), and generates the background image on the basis of a result of the subtraction. Therefore, it is possible to generate the background image from which the fluorescent component is removed.

Note that in the first embodiment, in order to generate the background image, the image processing unit 91 subtracts, from each of the second and third pixel values (pixel value of each of the G pixel and B pixel), the multiplication result obtained by multiplying the value obtained by dividing the spectral sensitivity of each of the second and third filters (filter G and filter B) to the fluorescence wavelength by the spectral sensitivity of the first filter (filter R) to the fluorescence wavelength by the first pixel value (pixel value of the R pixel), but the first pixel value may simply be used directly.

Furthermore, in the first embodiment, in a case where the medical observation system 1 is set to the fluorescence observation mode, the second control unit 94 causes each of the second light source unit 32 and the third light source unit 33 to emit light, but may causes at least one of the first light source unit 31, the second light source unit 32, and the third light source unit 33 to emit light for irradiation with the visible light. In this case, the image processing unit 91 desirably uses the pixel value of a pixel that has the highest sensitivity to the light emitted as the visible light to generate the background image, and uses the pixel values of the other pixels to generate the fluorescence image. Specifically, when the second light source unit 32 emits light as the visible light to irradiate the object to be observed with the green light, the image processing unit 91 desirably uses the pixel value of the G pixel contained in the image data input from the imaging unit 21 to generate the background image, and uses the pixel value of each of the R pixel and B pixel to generate the fluorescence image.

Furthermore, in the first embodiment, the image processing unit 91 performs the grayscale processing on the background image, but may perform the grayscale processing on the fluorescence image, or may perform the grayscale processing on each of the background image and fluorescence image. Therefore, it is possible to enhance the fluorescent area on the composite image. As a matter of course, the image processing unit 91 may omit the grayscale processing for each of the background image and the fluorescence image. Therefore, it is possible to simplify the processing.

Furthermore, in the first embodiment, the image processing unit 91 performs the monochromatization for the fluorescence image, but may perform the colorization for the background image or may perform the colorization for each of the background image and the fluorescence image. In this case, the image processing unit 91 performs colorization for each of the background image and the fluorescence image so that the background image and the fluorescence image may have different colors. Therefore, it is possible to enhance the fluorescent area on the composite image. As a matter of course, the image processing unit 91 may omit the colorization for each of the background image and the fluorescence image. Therefore, it is possible to simplify the processing.

Furthermore, in the first embodiment, the first light source unit 31, the second light source unit 32, and the fourth light source unit 34 are caused to emit light in the fluorescence observation mode, but, for example, a light source configured to emit white light and a cut filter configured to block a blue wavelength band and transmit light in the other wavelength bands may be provided to arrange the cut filter on a white-light optical path along which the white light is emitted, in the fluorescence observation mode. As a matter of course, the cut filter having a transmission characteristic of blocking the green wavelength band but transmitting light in the other wavelength bands may be applied.

Furthermore, in the first embodiment, the cut filter blocking the green or blue wavelength band and transmitting light in the other wavelength bands can be removably provided on the optical path between the optical system 211 and the cut filter 213, and thus, the cut filter can be applied so as to be inserted in the optical path between the optical system 211 and the cut filter 213, in the fluorescence observation mode.

Furthermore, in the first embodiment, in a case where the image processing unit 91 generates the composite image by using the fluorescence image and the background image, a portion of the fluorescence image having the brightness value equal to or larger higher than a predetermined value may be combined with the background image to generate the composite image. Therefore, it is possible to further enhance the fluorescent area.

(Modification of First Embodiment)

Next, a modification of the first embodiment will be described. In the first embodiment described above, an image is captured by one image sensor 212 (single plate) having the Bayer array, but in the modification of the first embodiment, a plurality of image sensors is used.

Figure 12:
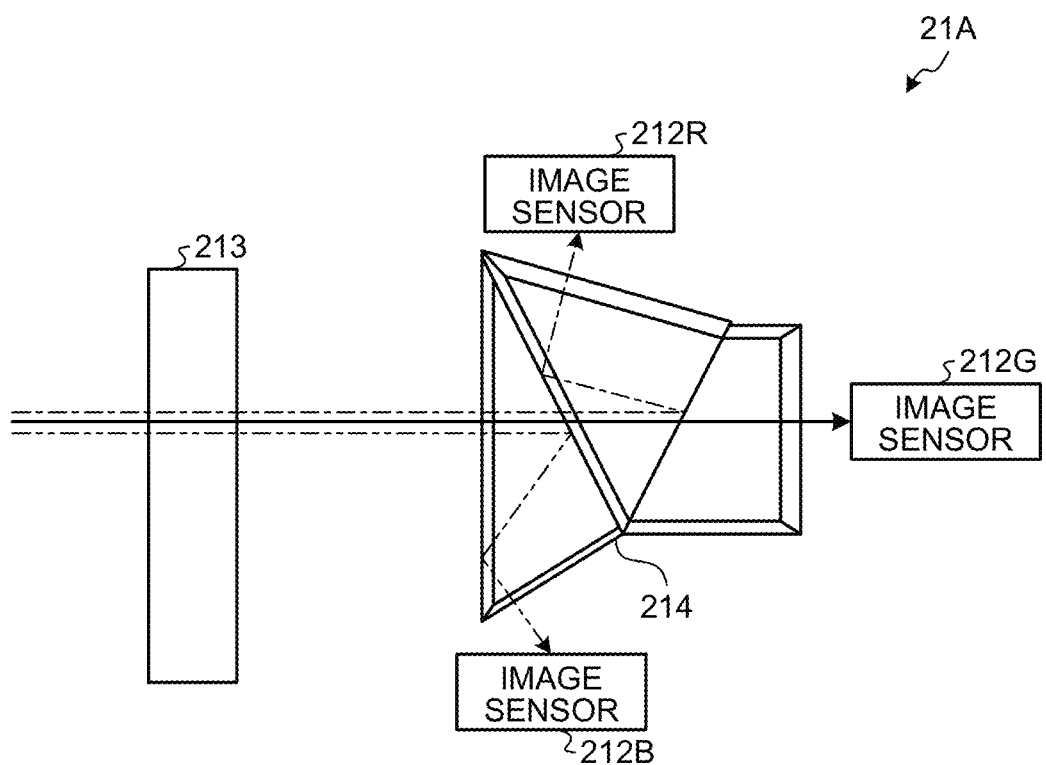
FIG. 12 is a conceptual diagram illustrating a configuration of an imaging unit according to a modification of the first embodiment.

FIG. 12 is a conceptual diagram illustrating a configuration of the imaging unit according to the modification of the first embodiment. The imaging unit 21 illustrated in FIG. 12 includes an image sensor 212R, an image sensor 212G, an image sensor 212B, and a dichroic prism 214, in place of the image sensor 212 described above.

The image sensor 212R includes the pixel portion 212a described above, receives red light split by the dichroic prism 214 which is described later, and performs photoelectric conversion to generate the image data.

The image sensor 212G includes the pixel portion 212a described above, receives green light split by the dichroic prism 214 which is described later, and performs photoelectric conversion to generate the image data.

The image sensor 212B includes the pixel portion 212a described above, receives blue light split by the dichroic prism 214 which is described later, and performs photoelectric conversion to generate the image data.

The dichroic prism 214 outputs red light and fluorescence of light that is input through the cut filter 213, to the image sensor 212R, outputs green light and fluorescence to the image sensor 212G, and outputs blue light and fluorescence to the image sensor 212B.

According to the modification of the first embodiment described above, the effects similar to those of the first embodiment described above can be obtained.

Second Embodiment

Next, a second embodiment will be described. In the first embodiment described above, the surgical microscope has been described as the medical observation system, but in the second embodiment, an endoscope system having a rigid endoscope will be described as the medical observation system. Note that the same configurations as those of the medical observation system 1 according to the first embodiment described above are denoted by the same reference numerals and symbols, and detailed description thereof will be omitted.

[Configuration of Medical Observation System]

Figure 13:
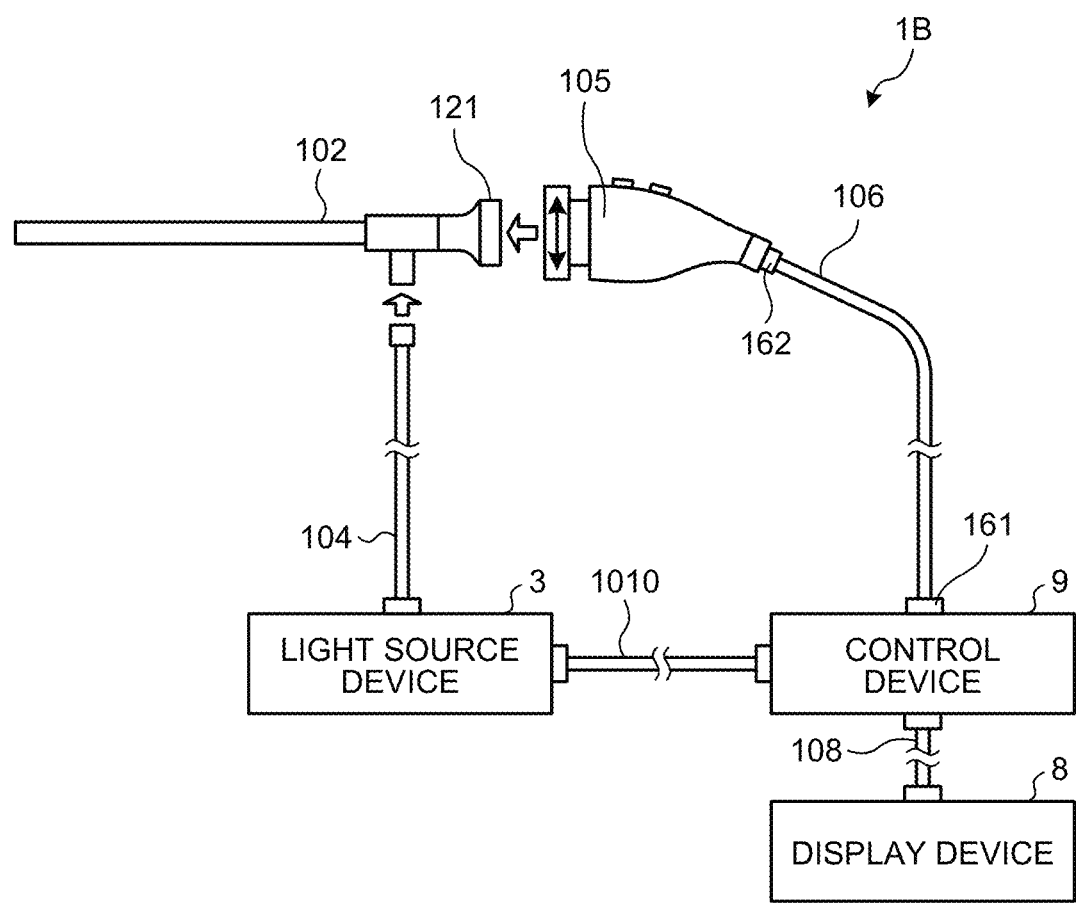
FIG. 13 is a diagram illustrating a schematic configuration of a medical observation system according to a second embodiment.

FIG. 13 is a diagram illustrating a schematic configuration of a medical observation system according to the second embodiment. A medical observation system 1B illustrated in FIG. 13 is used in the medical field and is a system configured to observe biological tissue in a subject such as a living body. Note that in the second embodiment, a rigid endoscope system using the rigid endoscope (insertion section 102) illustrated in FIG. 13 will be described, as the medical observation system 1B.

The medical observation system 1B illustrated in FIG. 13 includes the insertion section 102, the light source device 3, a light guide 104, an endoscope camera head 105 (endoscopic imaging device), a first transmission cable 106, the display device 8, a second transmission cable 108, the control device 9, and a third transmission cable 1010.

The insertion section 102 is rigid or at least partially flexible and has an elongated shape. The insertion section 102 is inserted into the subject such as a patient, through a trocar. The insertion section 102 is internally provided with an optical system, such as a lens, configured to form an observation image.

The light guide 104 has one end that is detachably connected to the light source device 3 and the other end that is detachably connected to the insertion section 102. The light guide 104 guides illumination light supplied from the light source device 3 from the one end to the other end and supplies the illumination light to the insertion section 102.

The insertion section 102 includes an eyepiece 121 that is detachably connected to the endoscope camera head 105. Under the control of the control device 9, the endoscope camera head 105 receives the observation image formed by the insertion section 102, performs photoelectric conversion to generate image data (RAW data), and outputs the image data to the control device 9 via the first transmission cable 106.

The first transmission cable 106 has one end that is detachably connected to the control device 9 through a video connector 161, and the other end that is connected to the endoscope camera head 105 through a camera head connector 162. The first transmission cable 106 transmits the image data output from the endoscope camera head 105 to the control device 9 and transmits setting data, power, or the like output from the control device 9, to the endoscope camera head 105.

The second transmission cable 108 has one end that is detachably connected to the display device 8, and the other end that is detachably connected to the control device 9. The second transmission cable 108 transmits the image data subjected to image processing by the control device 9, to the display device 8.

The third transmission cable 1010 has one end that is detachably connected to the light source device 3, and the other end that is detachably connected to the control device 9. The third transmission cable 1010 transmits control data from the control device 9 to the light source device 3.

[Functional Configuration of Main Portion of Medical Observation System]

Figure 14:
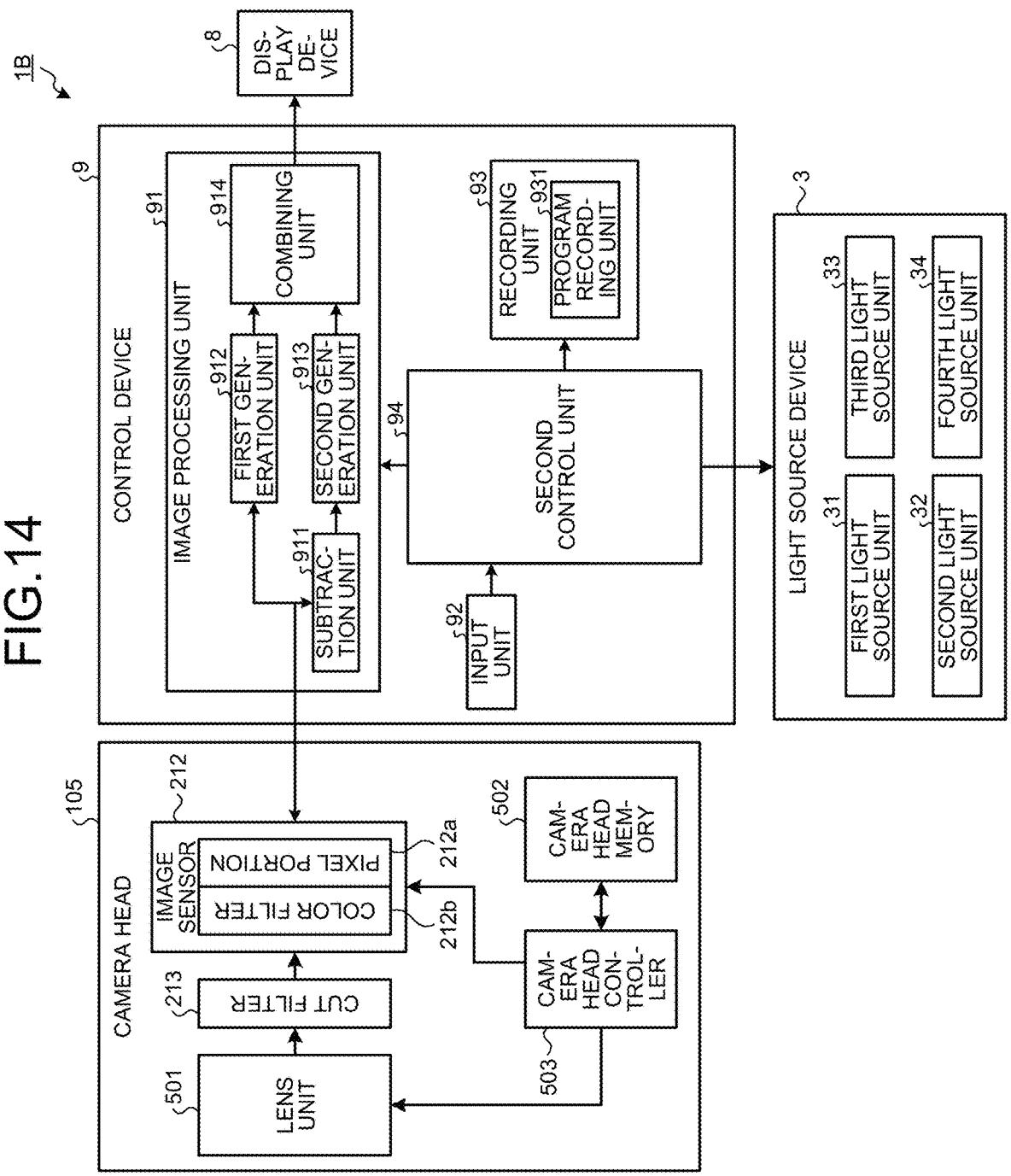
FIG. 14 is a block diagram illustrating a functional configuration of a main portion of the medical observation system according to the second embodiment.

Next, a functional configuration of a main portion of the medical observation system 1B described above will be described. FIG. 14 is a block diagram illustrating the functional configuration of the main portion of the medical observation system 1B.

[Configuration of Endoscope Camera Head]

First, a configuration of the endoscope camera head 105 will be described. The endoscope camera head 105 includes the image sensor 212, the cut filter 213, a lens unit 501, a camera head memory 502, and a camera head controller 503.

The lens unit 501 forms an object image focused by the optical system of the insertion section 102, on a light receiving surface of the image sensor 212. The focal position of the lens unit 501 is changeable. The lens unit 501 includes a plurality of lenses.

The camera head memory 502 records various types of information about the endoscope camera head 105 (e.g., pixel information about the image sensor 212 and characteristics of the cut filter 213). Furthermore, the camera head memory 502 records various setting data and control parameters transmitted from the control device 9 through the first transmission cable 106. The camera head memory 502 includes a non-volatile memory or a volatile memory.

The camera head controller 503 controls the operation of each unit constituting the endoscope camera head 105, on the basis of the setting data received from the control device 9 through the first transmission cable 106. The camera head controller 503 is implemented by using a timing generator (TG), a processor that is a processing device having hardware such as CPU, and a memory that is a temporary storage area used by the processor.

The medical observation system 1B having such a configuration performs processing similar to the processing performed by the medical observation system 1 described above (see FIG. 6).

According to the second embodiment described above, the effects similar to those of the first embodiment described above can be obtained, reducing the size of the endoscope camera head 105.

Third Embodiment

Next, a third embodiment will be described. In the third embodiment, a medical observation system that is applied to a flexible endoscope system using a flexible endoscope will be described. Note that the same configurations as those of the medical observation system 1 according to the first embodiment described above are denoted by the same reference numerals and symbols, and detailed description thereof will be omitted.

[Schematic Configuration of Medical Observation System]

Figure 15:
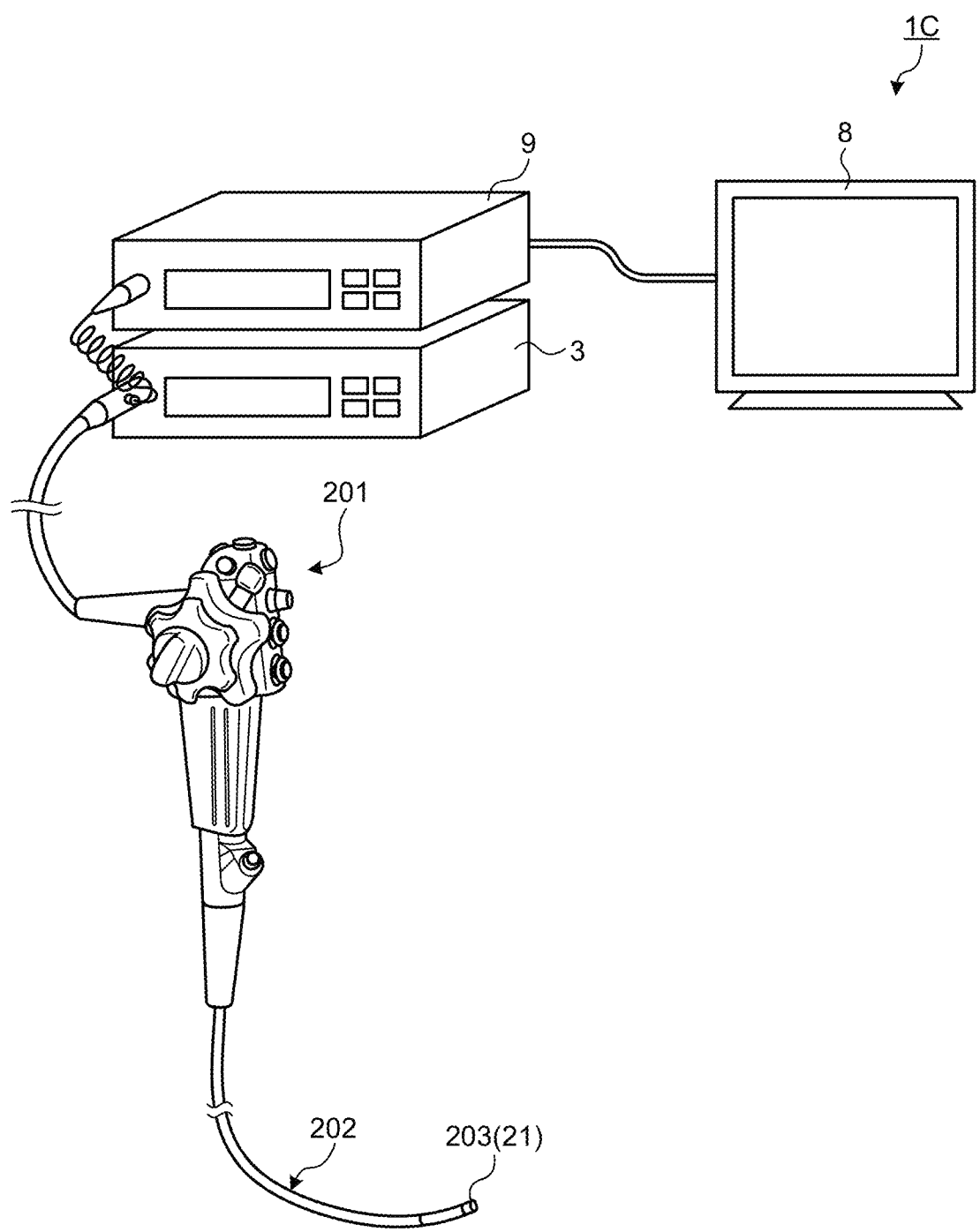
FIG. 15 is a diagram illustrating a schematic configuration of a medical observation system according to a third embodiment.

FIG. 15 is a diagram illustrating a schematic configuration of the medical observation system according to the third embodiment. A medical observation system 1C illustrated in FIG. 15 is inserted into a subject, images the inside of the subject to generate image data, and displays an image based on the image data.

As illustrated in FIG. 15, the medical observation system 1C includes an endoscope 201 that captures an in-vivo image of an observed region by inserting an insertion section 202 into the subject to generate the image data, the light source device 3, the display device 8, and the control device 9. The endoscope 201 is provided with the imaging unit 21 at a distal end portion 203 of the insertion section 202.

The medical observation system 1C having such a configuration performs processing similar to the processing performed by the medical observation system 1 described above (see FIG. 6).

According to the third embodiment described above, even if the medical observation system 1C including the flexible endoscope 201 is used, the effects similar to those of the first embodiment described above can be obtained.

Other Embodiments

Various aspects of the invention can be embodied by appropriately combining a plurality of component elements disclosed in the medical observation system according to the first to third embodiments of the present disclosure described above. For example, some component elements may be eliminated from all the component elements described in the medical observation system according to the first to third embodiments of the present disclosure described above. Furthermore, the component elements described in the medical observation system according to the embodiments of the present disclosure described above may be appropriately combined.

Furthermore, in the medical observation system according to the first to third embodiments of the present disclosure, the word "unit" described above can be read as "means", "circuit", or the like. For example, the control unit can be read as control means or a control circuit.

Furthermore, programs executed by the medical observation system according to the first to third embodiments of the present disclosure are provided in the form of installable or executable file data and recorded in a computer-readable recording medium, such as a CD-ROM, flexible disk (FD), CD-R, digital versatile disk (DVD), USB medium, or flash memory.

Alternatively, the programs executed by the medical observation system according to the first to third embodiments of the present disclosure may be configured to be stored on a computer connected to a network such as the Internet and provided by being downloaded via the network.

It is noted that, in the description of the flowchart herein, the context between sequential timings of the processing has been clearly shown by using expressions, such as "first", "then", and "next", but the order of the processes of the processing necessary to embody the present disclosure is not uniquely defined by these expressions. In other words, the order of the processes of the processing in the flowchart described herein may be changed within a consistent range. For example, the generation and colorization of the fluorescence image and the generation and grayscale processing of the background image can be performed in parallel.

Some embodiments of the present application have been described in detail with reference to the drawings, but these are provided by way of examples, and it is possible to embody other aspects of the present invention to which various modifications and improvements are made on the basis of the knowledge of those skilled in the art, in addition to the aspects described in the present disclosure.

Note that the present technology can also have the following configurations.

(Additional Note 1)

A medical observation system including: a light source device configured to emit, to an object, first visible light and second visible light having different wavelength bands, and excitation light exciting a fluorescent substance and causing emission of fluorescence;

an image sensor including: a pixel portion including a plurality of pixels; a first filter configured to transmit the first visible light and the fluorescence; and a second filter configured to transmit the second visible light and the fluorescence, each of the first filter and the second filter being provided on a light receiving surface of each of the plurality of pixels, the image sensor being configured to capture at least one of reflected light of at least one of the first visible light and the second visible light reflected from the object and the fluorescence to generate image data;

a control unit configured to control the light source device to simultaneously emit the second visible light and the excitation light; and an image processing unit configured to generate a fluorescence image based on a first pixel value included in the image data and output from a pixel in which the first filter is arranged, and a background image based on a second pixel value output from a pixel in which the second filter is arranged.

(Additional Note 2)

The medical observation system according to (Additional Note 1), including a cut filter provided on an incident side of the image sensor and configured to transmit the reflected light and the fluorescence while blocking the excitation light.

(Additional Note 3)

The medical observation system according to (Additional Note 1) or (Additional Note 2), wherein the image processing unit is configured to change the second pixel value based on the first pixel value, and generate the background image based on the changed second pixel value.

(Additional Note 4)

The medical observation system according to (Additional Note 3), wherein the image processing unit is configured to subtract the first pixel value from the second pixel value, and generate the background image based on a result of subtraction.

(Additional Note 5)

The medical observation system according to any one of (Additional Note 1) to (Additional Note 4), wherein the image processing unit is configured to subtract, from the second pixel value, a multiplication result obtained by multiplying a value obtained by dividing a spectral sensitivity of the second filter to a fluorescence wavelength by a spectral sensitivity of the first filter to the fluorescence wavelength by the first pixel value, and generate the background image based on a result of subtraction.

(Additional Note 6)

The medical observation system according to any one of (Additional Note 1) to (Additional Note 5), wherein the control unit is configured to control, in a first observation mode, the light source device to emit the first visible light and the second visible light, and control, in a second observation mode, the light source device to emit the second visible light and the excitation light.

(Additional Note 7)

The medical observation system according to any one of (Additional Note 1) to (Additional Note 6), wherein the light source device is configured to emit third visible light having a wavelength band different from those of the first visible light and the second visible light, the image sensor includes a third filter configured to transmit the third visible light and the fluorescence, and the image sensor is configured to generate the background image based on a third pixel value output from a pixel in which the third filter is arranged and the second pixel value, the third pixel value and the second pixel value being included in image data.

(Additional Note 8)

The medical observation system according to (Additional Note 7), wherein the first visible light is light in a red wavelength band, the second visible light is one of light in a green wavelength band and light in a blue wavelength band, the third visible light is the other of the light in a green wavelength band and the light in a blue wavelength band, the first filter is a red filter configured to transmit the light in a red wavelength band and the fluorescence, the second filter is one of a green filter and a blue filter configured to transmit one of the light in a green wavelength band and the light in a blue wavelength band, and further to transmit the fluorescence, and the third filter is the other of the green filter and the blue filter configured to transmit other of the light in a green wavelength band and the light in a blue wavelength band, and further to transmit the fluorescence.

(Additional Note 9)

The medical observation system according to (Additional Note 8), wherein the light source device includes:

a first light source unit configured to emit the light in a red wavelength band;

a second light source unit configured to emit the light in a green wavelength band;

a third light source unit configured to emit the light in a blue wavelength band; and a fourth light source unit configured to emit the excitation light, and the control unit is configured to control the first light source unit, the second light source unit, and the third light source unit to emit light, in a white light observation mode for observation with white light, and control the second light source unit, the third light source unit, and the fourth light source unit to emit light, in a fluorescence observation mode for observation of the fluorescence.

(Additional Note 10)

The medical observation system according to any one of (Additional Note 1) to (Additional Note 9), wherein the image processing unit is configured to generate a composite image in which the background image and the fluorescence image are combined.

(Additional Note 11)

The medical observation system according to any one of (Additional Note 1) to (Additional Note 9), wherein the image processing unit is configured to perform grayscale processing on at least one of the background image and the fluorescence image.

(Additional Note 12)

The medical observation system according to any one of (Additional Note 1) to (Additional Note 9), wherein the image processing unit is configured to perform colorization on at least one of the background image and the fluorescence image.

(Additional Note 13)

The medical observation system according to any one of (Additional Note 1) to (Additional Note 12), wherein the fluorescent substance is indocyanine green, and the excitation light has a center wavelength of 740 nm.

(Additional Note 14)

A medical observation system including:

a light source device configured to emit, to an object, first visible light and second visible light having different wavelength bands, and excitation light exciting a fluorescent substance and causing emission of fluorescence;

a dichroic prism configured to split reflected light of at least one of the first visible light and the second visible light reflected from the object and the fluorescence into a plurality of wavelength bands;

a plurality of image sensors configured to receive light beams of the plurality of wavelength bands split by the dichroic prism and generate a plurality of pieces of image data;

a control unit configured to control the light source device to simultaneously emit the second visible light and the excitation light; and an image processing unit configured to generate a background image and a fluorescence image based on the plurality of pieces of image data.

(Additional Note 15)

The medical observation system according to any one of (Additional Note 1) to (Additional Note 14) further including:

a support unit configured to turnably support a medical imaging device including the image sensor; and a base portion configured to turnably hold a base end portion of the support unit, the base portion being movable on a floor surface.

(Additional Note 16)

The medical observation system according to any one of (Additional Note 1) to (Additional Note 14) further including an insertion section configured to be insertable into a subject and including an optical system focusing the reflected light and the fluorescence to form an object image on a light receiving surface of the image sensor.

(Additional Note 17)

The medical observation system according to (Additional Note 16), wherein the insertion section is detachable from a medical imaging device including the image sensor.

(Additional Note 18)

A control device for controlling a light source device and a medical imaging device, the light source device being configured to emit, to an object, first visible light and second visible light having different wavelength bands, and excitation light exciting a fluorescent substance and causing emission of fluorescence, the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, the control device including:

a control unit configured to control the light source device to simultaneously emit the second visible light and the excitation light; and an image processing unit configured to generate a fluorescence image based on a first pixel value included in the image data and output from a pixel in which the first filter is arranged, and a background image based on a second pixel value output from a pixel in which the second filter is arranged.

(Additional Note 19)

A control method executed by a control device for controlling a light source device and a medical imaging device, the light source device being configured to emit, to an object, first visible light and second visible light having different wavelength bands, and excitation light exciting a fluorescent substance and causing emission of fluorescence, the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, the control method including:

controlling the light source device to simultaneously emit the second visible light and the excitation light; and generating a fluorescence image based on a first pixel value included in the image data and output from a pixel in which the first filter is arranged, and a background image based on a second pixel value output from a pixel in which the second filter is arranged.

REFERENCE SIGNS LIST 1, 1B, 1C MEDICAL OBSERVATION SYSTEM
2 OBSERVATION APPARATUS
3 LIGHT SOURCE DEVICE
4 LIGHT GUIDE
5 MICROSCOPE UNIT
6 SUPPORT UNIT
7 BASE PORTION
8 DISPLAY DEVICE
9 CONTROL DEVICE
21 IMAGING UNIT
22 LIGHT EMITTING UNIT
23 DETECTION UNIT
24 INPUT UNIT
25 FIRST CONTROL UNIT
31 FIRST LIGHT SOURCE UNIT
32 SECOND LIGHT SOURCE UNIT
33 THIRD LIGHT SOURCE UNIT
34 FOURTH LIGHT SOURCE UNIT
91 IMAGE PROCESSING UNIT
92 INPUT UNIT
93 RECORDING UNIT
94 SECOND CONTROL UNIT
102 INSERTION SECTION
104 LIGHT GUIDE
105 ENDOSCOPE CAMERA HEAD
106 FIRST TRANSMISSION CABLE
108 SECOND TRANSMISSION CABLE
121 EYEPIECE
161 VIDEO CONNECTOR
162 CAMERA HEAD CONNECTOR
201 ENDOSCOPE
202 INSERTION SECTION
203 DISTAL END PORTION
211 OPTICAL SYSTEM
212, 212B, 212G, 212R IMAGE SENSOR
212a PIXEL PORTION
212b COLOR FILTER
213 CUT FILTER
214 DICHROIC PRISM
501 LENS UNIT
502 CAMERA HEAD MEMORY
503 CAMERA HEAD CONTROLLER
911 SUBTRACTION UNIT
912 FIRST GENERATION UNIT
913 SECOND GENERATION UNIT
914 COMBINING UNIT
931 PROGRAM RECORDING UNIT
1010 THIRD TRANSMISSION CABLE
P1 FLUORESCENCE IMAGE
P2 BACKGROUND IMAGE
P3 COMPOSITE IMAGE
Q1 FLUORESCENT AREA

The invention claimed is:

1. A medical observation system comprising:
a light source device configured to emit, to an object, first visible light and second visible light having different wavelength bands, and excitation light exciting a fluorescent substance and causing emission of fluorescence;

an image sensor including: a pixel portion including a plurality of pixels; a first filter configured to transmit the first visible light and the fluorescence; and a second filter configured to transmit the second visible light and the fluorescence, each of the first filter and the second filter being provided on a light receiving surface of each of the plurality of pixels, the image sensor being configured to capture at least one of reflected light of at least one of the first visible light and the second visible light reflected from the object and the fluorescence to generate image data; and circuitry configured to control the light source device to simultaneously emit the second visible light and the excitation light; and generate a fluorescence image based on a first pixel value included in the image data and output from a pixel in which the first filter is arranged, subtract, from a second pixel value output from a pixel in which the second filter is arranged, a multiplication result obtained by multiplying a value obtained by dividing a spectral sensitivity of the second filter to a fluorescence wavelength by a spectral sensitivity of the first filter to the fluorescence wavelength by the first pixel value, and generate a background image based on a result of subtraction.

2. The medical observation system according to claim 1, comprising a cut filter provided on an incident side of the image sensor and configured to transmit the reflected light and the fluorescence while blocking the excitation light.

3. The medical observation system according to claim 1, wherein the circuitry is configured to change the second pixel value based on the first pixel value, and generate the background image based on the changed second pixel value.

4. The medical observation system according to claim 3, wherein the circuitry is configured to subtract the first pixel value from the second pixel value, and generate the background image based on a result of subtraction.

5. The medical observation system according to claim 1, wherein the circuitry is configured to control, in a first observation mode, the light source device to emit the first visible light and the second visible light, and control, in a second observation mode, the light source device to emit the second visible light and the excitation light.

6. The medical observation system according to claim 1, wherein the light source device is configured to emit third visible light having a wavelength band different from those of the first visible light and the second visible light, the image sensor includes a third filter configured to transmit the third visible light and the fluorescence, and the image sensor is configured to generate the background image based on a third pixel value output from a pixel in which the third filter is arranged and the second pixel value, the third pixel value and the second pixel value being included in image data.

7. The medical observation system according to claim 6, wherein the first visible light is light in a red wavelength band, the second visible light is one of light in a green wavelength band and light in a blue wavelength band, the third visible light is the other of the light in a green wavelength band and the light in a blue wavelength band, the first filter is a red filter configured to transmit the light in a red wavelength band and the fluorescence, the second filter is one of a green filter and a blue filter configured to transmit one of the light in a green wavelength band and the light in a blue wavelength band, and further to transmit the fluorescence, and the third filter is the other of the green filter and the blue filter configured to transmit other of the light in a green wavelength band and the light in a blue wavelength band, and further to transmit the fluorescence.

8. The medical observation system according to claim 7, wherein the light source device includes:

a first light source configured to emit the light in a red wavelength band;

a second light source configured to emit the light in a green wavelength band;

a third light source configured to emit the light in a blue wavelength band; and a fourth light source configured to emit the excitation light, and the circuitry is configured to control the first light source, the second light source, and the third light source to emit light, in a white light observation mode for observation with white light, and control the second light source, the third light source, and the fourth light source to emit light, in a fluorescence observation mode for observation of the fluorescence.

9. The medical observation system according to claim 1, wherein the circuitry is configured to generate a composite image in which the background image and the fluorescence image are combined.

10. The medical observation system according to claim 1, wherein the circuitry is configured to perform grayscale processing on at least one of the background image and the fluorescence image.

11. The medical observation system according to claim 1, wherein the circuitry is configured to perform colorization on at least one of the background image and the fluorescence image.

12. The medical observation system according to claim 1, wherein the fluorescent substance is indocyanine green, and the excitation light has a center wavelength of 740 nm.

13. The medical observation system according to claim 1 further comprising:

a support configured to turnably support a medical imaging device including the image sensor; and a base portion configured to turnably hold a base end portion of the support, the base portion being movable on a floor surface.

14. The medical observation system according to claim 1 further comprising an insertion section configured to be insertable into a subject and including an optical system focusing the reflected light and the fluorescence to form an object image on a light receiving surface of the image sensor.

15. The medical observation system according to claim 14, wherein the insertion section is detachable from a medical imaging device including the image sensor.

16. A medical observation system comprising:
a light source device configured to emit, to an object, first visible light and second visible light having different wavelength bands, and excitation light exciting a fluorescent substance and causing emission of fluorescence;
a dichroic prism configured to split reflected light of at least one of the first visible light and the second visible light reflected from the object and the fluorescence into a plurality of wavelength bands;
a plurality of image sensors configured to receive light beams of the plurality of wavelength bands split by the dichroic prism and generate a plurality of pieces of image data including a first piece of image data generated from the first visible light and the fluorescence and a second piece of image data generated the second visible light and the fluorescence;
circuitry configured to
control the light source device to simultaneously emit the second visible light and the excitation light;
generate a fluorescence image based on the plurality of pieces first piece of image data;
subtract, from the second piece of image data, a multiplication result obtained by multiplying a value obtained by dividing a spectral sensitivity to a fluorescence wavelength of a second surface of the dichroic prism that directs the second visible light to a corresponding sensor by a spectral sensitivity to the fluorescence wavelength of a first surface of the dichroic prism that directs the first visible light to a corresponding sensor; and
generate a background image based on a result of subtraction.

17. A control device for controlling a light source device and a medical imaging device,
the light source device being configured to emit, to an object, first visible light and second visible light having different wavelength bands, and excitation light exciting a fluorescent substance and causing emission of fluorescence,
the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, the control device comprising:
circuitry configured to
control the light source device to simultaneously emit the second visible light and the excitation light;
generate a fluorescence image based on a first pixel value included in the image data and output from a pixel in which the first filter is arranged;
subtract, from a second pixel value output from a pixel in which the second filter is arranged, a multiplication result obtained by multiplying a value obtained by dividing a spectral sensitivity of the second filter to a fluorescence wavelength by a spectral sensitivity of the first filter to the fluorescence wavelength by the first pixel value; and
generate a background image based on a result of subtraction.

18. A control method executed by a control device for controlling a light source device and a medical imaging device,
the light source device being configured to emit, to an object, first visible light and second visible light having different wavelength bands, and excitation light exciting a fluorescent substance and causing emission of fluorescence,
the medical imaging device including a pixel portion having a plurality of pixels, a first filter configured to transmit the first visible light and the fluorescence, and a second filter configured to transmit the second visible light and the fluorescence, each of the first filter and the second filter being provided on a light receiving surface of each of the plurality of pixels, the medical imaging device being configured to capture at least one of reflected light of at least one of the first visible light and the second visible light reflected from the object and the fluorescence to generate image data, the control method comprising:
controlling the light source device to simultaneously emit the second visible light and the excitation light;
generating a fluorescence image based on a first pixel value included in the image data and output from a pixel in which the first filter is arranged;
subtracting, from a second pixel value output from a pixel in which the second filter is arranged, a multiplication result obtained by multiplying a value obtained by dividing a spectral sensitivity of the second filter to a fluorescence wavelength by a spectral sensitivity of the first filter to the fluorescence wavelength by the first pixel value; and
generating a background image based on a result of subtraction.

19. The control method according to claim 18, further comprising performing colorization on at least one of the background image and the fluorescence image.

20. A non-transitory computer readable storage device having computer readable instructions that when executed by circuitry cause the circuitry to perform the control method of claim 18.

* * * * *